(12) United States Patent
Cantley et al.

(10) Patent No.: US 8,552,050 B2
(45) Date of Patent: Oct. 8, 2013

(54) ACTIVATORS OF PYRUVATE KINASE M2 AND METHODS OF TREATING DISEASE

(75) Inventors: Lewis C. Cantley, Cambridge, MA (US); Matthew G. Vander Heiden, Somerville, MA (US); Heather R. Christofk, Carlsbad, CA (US)

(73) Assignee: Beth Israel Deaconess Medical Center, Boston, MA (US)

( * ) Notice: Subject to any disclaimer, the term of this patent is extended or adjusted under 35 U.S.C. 154(b) by 493 days.

(21) Appl. No.: 12/672,827

(22) PCT Filed: Aug. 18, 2008

(86) PCT No.: PCT/US2008/009828
§ 371 (c)(1),
(2), (4) Date: Feb. 9, 2010

(87) PCT Pub. No.: WO2009/025781
PCT Pub. Date: Feb. 26, 2009

(65) Prior Publication Data
US 2011/0046083 A1    Feb. 24, 2011

Related U.S. Application Data

(60) Provisional application No. 61/065,758, filed on Feb. 14, 2008, provisional application No. 60/964,979, filed on Aug. 16, 2007.

(51) Int. Cl.
| | | |
|---|---|---|
| *A01N 43/56* | (2006.01) | |
| *A01N 43/08* | (2006.01) | |
| *A01N 37/10* | (2006.01) | |
| *A01N 41/06* | (2006.01) | |
| *A61K 31/415* | (2006.01) | |
| *A61K 31/34* | (2006.01) | |
| *A61K 31/19* | (2006.01) | |
| *A61K 31/18* | (2006.01) | |
| *C07D 231/00* | (2006.01) | |
| *C07D 307/02* | (2006.01) | |
| *C07C 63/04* | (2006.01) | |
| *C07C 303/00* | (2006.01) | |
| *C07C 307/00* | (2006.01) | |
| *C07C 309/00* | (2006.01) | |
| *C07C 311/00* | (2006.01) | |

(52) U.S. Cl.
USPC ........... 514/407; 514/461; 514/568; 514/604; 548/374.1; 549/502; 562/493; 564/87

(58) Field of Classification Search
USPC ............... 514/407, 461, 568, 604; 548/374.1; 549/502; 562/493; 564/87
See application file for complete search history.

(56) References Cited

U.S. PATENT DOCUMENTS

2004/0152648 A1    8/2004  Ullrich et al.
2004/0235755 A1 *  11/2004  Eigenbrodt et al. ............ 514/23

OTHER PUBLICATIONS http://www.thefreedictionary.com/prevent (date unknown).*
http://www.cancer.gov/cancertopics/types/alphalist/y (date unknown).*
http://info.cancerresearchuk.org/healthyliving/introducingcancerprevention/ (date unknown).*
Surh, Nature Reviews Cancer, 2003, Nature Publishing Group, vol. 3, pp. 768-780.*
Cuzick et. al., The Lancet, 2003, The Lancet Publishing Group, vol. 361, pp. 296-300.*
Schneider et. al., Cancer Letters, 2003, Elsevier, vol. 193, pp. 91-98.*
Pujol et. al., British Journal of Cancer, 2000, Cancer Research Campaign, vol. 83, issue 1, pp. 8-15.*
Clement et. al., Antioxidants and Redox Signaling, 2005, Mary Ann Liebert, vol. 7, issues 3-4, pp. 456-464.*
Chabner et. al., Nature Rev. Cancer, 2005, Nature Publishing Group, vol. 5, pp. 65-72.*
Rich et. al., Nature Rev. Drug Disc., 2004, Nature Publishing Group, vol. 3, pp. 430-446.*
Beger et. al., World J. Surg., 2003, Societe Internationale de Chirurgie, vol. 27, pp. 1075-1083.*
Budinger et al., "Cellular Energy Utilization and Supply During Hypoxia in Embryonic Cardiac Myocytes," *Am J Physiol.* 270: L44-53 (1996).
Christofk et al., "Pyruvate Kinase M2 is a Phosphotyrosine-Binding Protein," *Nature* 452: 181-186 (2008).
Christofk et al., "The M2 Splice Isoform of Pyruvate Kinase is Important for Cancer Metabolism and Tumour Growth," *Nature* 452: 230-233 (2008).
Dombrauckas et al., "Structural Basis for Tumor Pyruvate Kinase M2 Allosteric Regulation and Catalysis," *Biochemistry* 44: 9417-9429 (2005).
Eigenbrodt et al., "Double Role for Pyruvate Kinase Type $M_2$ in the Expansion of Phosphometabolite Pools Found in Tumor Cells," *Crit Rev Oncog.* 3: 91-115 (1992).
Engelman et al., "Allelic Dilution Obscures Detection of a Biologically Significant Resistance Mutation in EGFR-Amplified Lung Cancer," *J Clin Invest.* 116: 2695-2706 (2006).
Jurica et al., "The Allosteric Regulation of Pyruvate Kinase by Fructose-1,6-Bisphosphate," *Structure* 6: 195-210 (1998).
Kharalkar et al., "Identification of Novel Allosteric Regulators of Human-Erythrocyte Pyruvate Kinase," *Chem Biodivers.* 4: 2603-2617 (2007).

(Continued)

*Primary Examiner* — Sreeni Padmanabhan
*Assistant Examiner* — Sarah Pihonak
(74) *Attorney, Agent, or Firm* — Clark & Elbing LLP; Kristina Bieker-Brady

(57) ABSTRACT

The invention described herein features methods, compositions, and kits for the use of activators of PKM2 for the treatment, prevention, or amelioration of diseases related to PKM2 function, including, e.g., cancer, diabetes, atherosclerosis, restenosis, obesity, autoimmune disorders, and proliferative disorders.

4 Claims, 16 Drawing Sheets

(56) References Cited

OTHER PUBLICATIONS

Root et al., "Genome-Scale Loss-of-Function Screening with a Lentiviral RNAi Library," *Nat Methods* 3: 715-719 (2006).
Sabatine et al., "Metabolomic Identification of Novel Biomarkers of Myocardial Ischemia," *Circulation* 112: 3868-3875 (2005).
Vander Heiden et al., "Growth Factors Can Influence Cell Growth and Survival Through Effects on Glucose Metabolism," *Mol Cell Biol.* 21: 5899-5912 (2001).
Villén et al., "Large-Scale Phosphorylation Analysis of Mouse Liver," *Proc Natl Acad Sci USA* 104: 1488-1493 (2007).
Yamada and Noguchi, "Nutrient and Hormonal Regulation of Pyruvate Kinase Gene Expression," *Biochem J.* 337: 1-11 (1999).
International Preliminary Report on Patentability for PCT/US2008/009828, dated Feb. 16, 2010.
International Search Report for PCT/US2008/009828, dated Dec. 5, 2008.
Written Opinion of the International Searching Authority for PCT/US2008/009828, dated Dec. 5, 2008.

\* cited by examiner a c

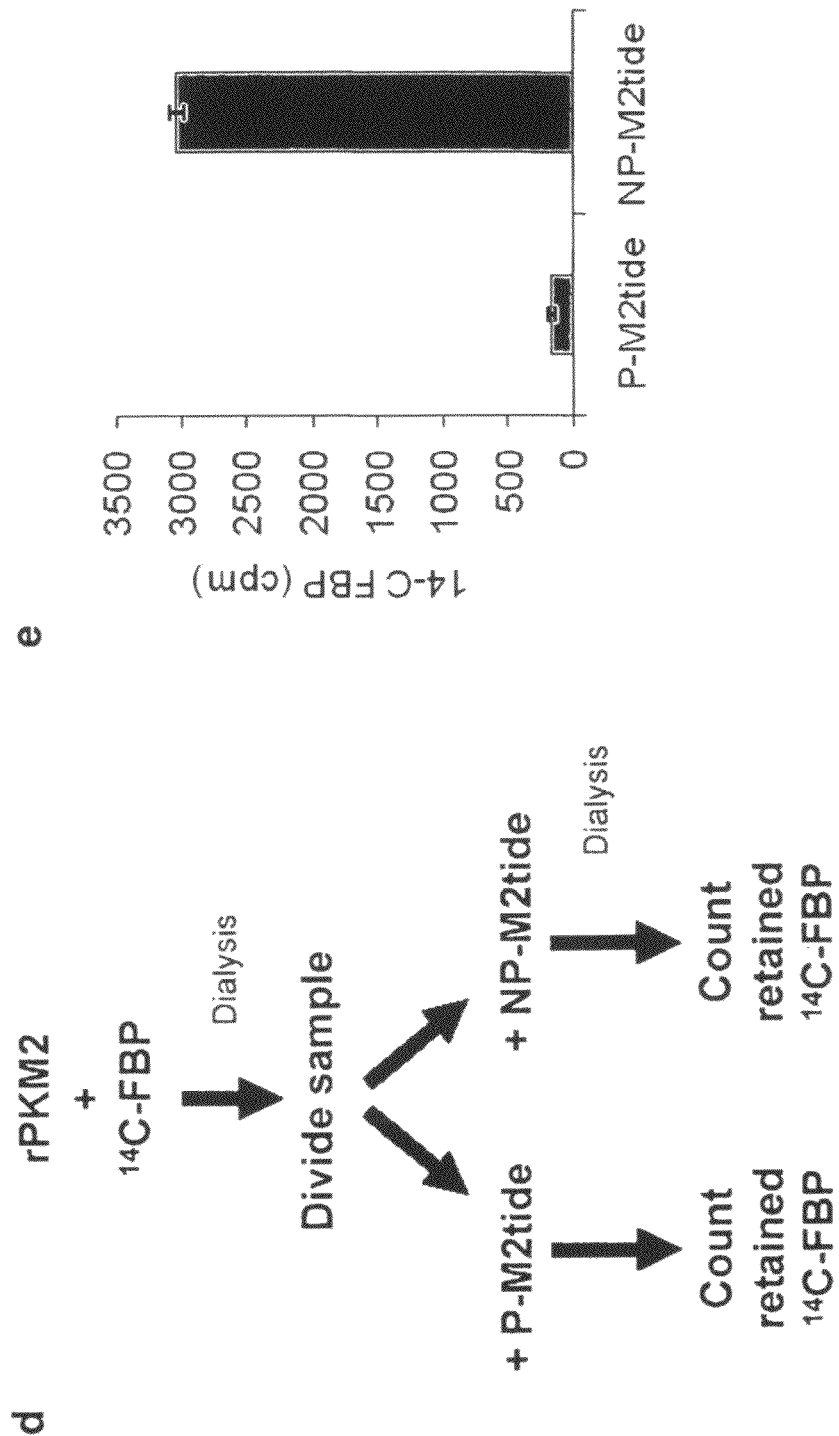

Figure 5

| -3 | -2 | -1 | pY | +1 | +2 | +3 | +4 | +5 |
|---|---|---|---|---|---|---|---|---|
| D (1.9) | D (1.8) | D (1.6) | X | | T (1.5) | F (1.7) | X | N (1.5) |
| N (1.5) | N (1.5) | N (1.5) | | | Q (1.5) | Y (1.7) | | T (1.5) |
| Q (1.4) | Q (1.5) | Q (1.5) | | | S (1.4) | I (1.5) | | S (1.4) |
| T (1.4) | T (1.4) | S (1.4) | | | N (1.2) | L (1.5) | | Q (1.4) |
| S (1.3) | S (1.4) | T (1.3) | | | | | | |

P-M2tide:   GGAVDDDpYAQFANGG
NP-M2tide:  GGAVDDDYAQFANGG g

ACTIVATORS OF PYRUVATE KINASE M2 AND METHODS OF TREATING DISEASE

CROSS-REFERENCE TO RELATED APPLICATIONS

This application is the U.S. National Stage of International Application No. PCT/US2008/009828, filed on Aug. 18, 2008, which claims the benefit of U.S. Provisional Application Ser. Nos. 60/964,979, filed on Aug. 16, 2007, and 61/065,758, filed on Feb. 14, 2008.

STATEMENT AS TO FEDERALLY FUNDED RESEARCH

The United States Government has a paid-up license in this invention and the right in limited circumstances to require the patent owner to license others on reasonable terms as provided for by the terms of R01 GM56203 awarded by the National Institute of Health (NIH).

BACKGROUND OF THE INVENTION

The invention described herein features methods, compositions, and kits that utilize activators of pyruvate kinase M2 (PKM2) for the treatment, prevention, or amelioration of diseases related to PKM2 function, including, e.g., cancer, diabetes, atherosclerosis, restenosis, obesity, autoimmune disorders, and proliferative disorders.

Cancer cells rely primarily on glycolysis to generate cellular energy, while the majority of "normal" cells in adult tissues utilize aerobic respiration. This fundamental difference in cellular metabolism between cancer cells and normal cells, termed aerobic glycolysis or the Warburg Effect, has been exploited for diagnostic purposes, but has not yet been exploited for therapeutic benefit.

Pyruvate kinase (PK) is a metabolic enzyme that converts phosphoenolpyruvate to pyruvate during glycolysis. Four PK isoforms exist in mammals: the L and R isoforms are expressed in liver and red blood cells, respectively, the M1 isoform is expressed in most adult tissues, and the M2 isoform is a splice variant of M1 expressed during embryonic development. All tumor cells exclusively express the embryonic M2 isoform. A well-known difference between the M1 and M2 isoforms of PK is that M2 is a low-activity enzyme that relies on allosteric activation by the upstream glycolytic intermediate, fructose-1,6-bisphosphate (FBP), whereas M1 is a constitutively active enzyme.

SUMMARY OF THE INVENTION

The invention features methods, compositions, and kits that utilize activators of pyruvate kinase M2 (PKM2) for the treatment, prevention, or amelioration of a disorder or disease related to PKM2 function.

Accordingly, in one aspect, the invention features a method of increasing the level of PKM2 activity and/or glycolysis (e.g., inhibiting the endogenous ability of a cell in the patient to down regulate PKM2) in a patient in need thereof. The method comprises the step of administering an effective amount of an activator, preferably a selective activator, of PKM2 to the patient in need thereof, thereby increasing the level of PKM2 activity and/or glycolysis in the patient. PKM2 is only expressed in growing cells such as cancer cells or fat cells in the patient; other tissues use other isoforms of PK. In embodiments of the invention, an activator is used to maintain PKM2 in its active conformation or constitutively activate pyruvate kinase activity in proliferating cells as a means to divert glucose metabolites into catabolic rather than anabolic processes in the patient.

In another aspect, the invention features a method of regulating cell proliferation in a patient in need thereof. The method comprises the step of administering an effective amount of an activator, preferably a selective activator, of PKM2 to the patient in need thereof, thereby regulating cell proliferation in the patient. This method can inhibit growth of a transformed cell, e.g., a cancer cell, or generally inhibit growth in a PKM2-dependent cell that undergoes aerobic glycolysis.

In another aspect, the invention features a method of treating a patient suffering from or susceptible to a disease or disorder associated with the function of PKM2. The method comprises the step of administering an effective amount of an activator, preferably a selective activator, of PKM2 to the patient in need thereof, thereby treating, preventing, or ameliorating the disease or disorder in the patient. In another embodiment, the activator is provided in a pharmaceutical composition.

In another embodiment, the method includes identifying or selecting a patient who would benefit from activation of PKM2. The patient can be identified on the basis of the level of PKM2 activity in a cell of the patient (e.g., as opposed to merely being in need of treatment of the disorder (e.g., cancer)). In another embodiment, the selected patient is a patient suffering from or susceptible to a disorder or disease identified herein, e.g., a disorder characterized by unwanted cell growth or proliferation, e.g., cancer, obesity, diabetes, atherosclerosis, restenosis, and autoimmune diseases.

In another embodiment, the activator of PKM2 utilized in the methods and compositions of this invention operates by or has one or more of the following mechanisms or properties: the activator is an allosteric activator of PKM2; the activator stabilizes the binding of FBP in a binding pocket of PKM2; the activator inhibits the release of FBP from a binding pocket of PKM2; the activator is an agonist, e.g., an analog, of FBP, e.g., an agonist which binds PKM2 with a lower, about the same, or higher affinity than does FBP; the activator inhibits the dissolution of tetrameric PKM2; the activator promotes the assembly of tetrameric PKM2; the activator stabilizes the tetrameric conformation of PKM2; the activator inhibits the binding of a phosphotyrosine containing polypeptide to PKM2; the activator inhibits the ability of a phosphotyrosine containing polypeptide to induce the release of FBP from PKM2, e.g., by inducing a change in the conformation of PKM2, e.g., in the position of Lys433, thereby hindering the release of FBP; the activator binds to or changes the position of Lys433 relative to the FBP binding pocket; the activator selectively activates PKM2 over at least one other isoform of PK, e.g., the activator is selective for PKM2 over one or more of PKR, PKM1, or PKL; the activator has an affinity for PKM2 which is greater than its affinity for at least one other isoform of PK, e.g., PKR, PKM1, or PKL; the activator has an $EC_{50}$ of from about 100 micromolar to about 0.1 nanomolar, e.g., about 10 micromolar to about 0.1 nanomolar, about 1 micromolar to about 0.1 nanomolar, about 500 nanomolar to about 0.1 nanomolar, about 250 nanomolar to about 0.1 nanomolar, about 100 nanomolar to about 0.1 nanomolar, about 50 nanomolar to about 0.1 nanomolar, about 25 nanomolar to about 0.1 nanomolar, about 10 nanomolar to about 0.1 nanomolar, about 100 nanomolar to about 1 nanomolar, about 50 nanomolar to about 1 nanomolar, about 25 nanomolar to about 1 nanomolar, about 10 nanomolar to about 1 nanomolar; and/or the activator is provided at a dosage of 0.1 mg to about 3000 mg per day, e.g., about 1 mg to about 2400, about 15 mg to about 2400, about 15 mg to about 1500, about 75 mg to about 1200, or about 75 mg to about 600 mg per day.

In another embodiment, the activator is administered at a dosage and frequency sufficient to increase lactate production or oxidative phosphorylation.

The method may further include the step of co-administering to the patient in need thereof an additional therapeutic agent. The term "co-administering" as used herein means that an additional therapeutic agent may be administered together with an activator of this invention as part of a single dosage form or as separate, multiple dosage forms. Alternatively, the additional agent may be administered prior to, consecutively with, or following the administration of a PKM2 activator. In such combination therapy treatment, both the PKM2 activator and the additional therapeutic agent(s) are administered by conventional methods. The administration of a composition of this invention, comprising both a PKM2 activator and an additional therapeutic agent, to a patient does not preclude the separate administration of that same therapeutic agent, any other second therapeutic agent, or the same or different PKM2 activator to the patient at another time during a course of treatment.

When the treatment is for cancer, the additional therapeutic agent may be a chemotherapeutic agent. When the treatment is for an autoimmune disorder, the additional therapeutic agent may be an immune modulatory agent. When the treatment is for obesity, the additional therapeutic agent may be a metabolic modulator. When the treatment is for diabetes, the additional therapeutic agent can be an anti-diabetes drug, e.g., an oral anti-diabetes drug, e.g., metformin, insulin, or an insulin analog or derivative. The choice of an additional therapeutic agent will be based upon the disease or condition that the patient is suffering from or susceptible to, as well as the judgment of the treating physician In another embodiment, the patient is treated with a PKM2 activator without co-administration of a hypoxic cell sensitizer, e.g., tirapazamine.

In another embodiment, the patient is being treated for cancer is characterized by one or more of the following: cells in the cancer carry out aerobic glycolysis; the cancer tissue has increased glucose uptake, as compared to a control value for glucose uptake, e.g., as measured by 2-deoxyglucose uptake or uptake by a labeled glucose or glucose analog; the cancer is metastatic; the cancer is PET positive; or the cancer has increased PKM2 expression.

In another embodiment, the activator is administered at least twice. In still another embodiment, the activator is administered in sufficient amount and with sufficient frequency that therapeutic levels are maintained for at least 1, 3, 5, 7, 10, 20, 30, 60, or 180 days. In another embodiment, the treatment is pulsatile or repeated and each administration provides therapeutic levels that are maintained for at least 1, 3, 5, 7, 10, or 20 days.

In some specific embodiments, the additional therapeutic agent is an inhibitor of glutamine metabolism.

The invention described herein further features a pharmaceutical composition for the treatment, prevention, or amelioration of a disease associated with the function of PKM2, which comprises an activator of PKM2 activity (e.g., a selective activator of PKM2) and a pharmaceutically acceptable carrier. The activator is present in an amount that, when administered to a patient, is sufficient to treat a disease in a patient. The composition may be formulated as, e.g., a pill, a powder, a granulate, a suspension, an emulsion, a solution, a gel, a paste, an ointment, a cream, a foam, a lotion, a plaster, a suppository, an enema, an injectable, an implant, a spray, or an aerosol. The composition may be, e.g., formulated for targeted delivery or for extended or delayed release. The composition may be, e.g., formulated for oral, buccal, topical, rectal, subcutaneous, vaginal, inhalation, ophthalmic, parenteral, intravenous, or intramuscular administration.

In some embodiments, the pharmaceutical composition further comprises an additional therapeutic agent useful in the treatment of a patient suffering from or susceptible to a disease or condition selected from cancer, atherosclerosis, restenosis, an autoimmune disorder, a proliferative disorder, or obesity. In a more specific embodiment, the additional therapeutic agent is selected from a chemotherapeutic agent, an immune modulatory agent, a metabolic modulator, an anti-diabetes drug, insulin, or an insulin analog or derivative.

The invention described herein features a kit that includes a pharmaceutical composition containing a PKM2 activator and instructions for administering the composition to a patient having a disease associated with the function of PKM2. The kit may further include an additional therapeutic agent. The additional therapeutic agent will be appropriate for the disease or condition to be treated by the kit, and may be selected, e.g., from any of the additional therapeutic agents set forth above for combination therapies.

In another aspect, the invention features a method for evaluating a candidate compound for the ability to activate PKM2. The method includes providing a PKM2 polypeptide which includes at least the FBP binding region of PKM2; contacting the PKM2 polypeptide and the candidate compound; assessing the ability of the candidate compound to activate PKM2; and optionally, determining if the candidate compound binds to PKM2, thereby evaluating a candidate compound for the ability to activate PKM2.

In another embodiment the ability of the compound to activate PKM1, PKR, or PKL is determined and compared with the ability of the candidate compound to activate PKM2.

In another embodiment, the PKM2 polypeptide is a polypeptide present in human PKM2. It can include one or more of the following human PKM2 amino acids: Thr432, Lys433, Ser434, Ser437, Trp482, Arg489, Gly514, Gly518, Ser519, Gly520, and Phe521 (e.g., residues identified by crystallographic studies that form salt bridges and hydrogen bonds with FBP), and/or K433, D488, R489, R455, T454, T434, and N456 (e.g., residues that potentially define the phosphotyrosine binding pocket). In another embodiment, the polypeptide includes all or a portion of the PKM2 sequence from T432-G514. In other preferred embodiments, the PKM2 polypeptide includes sufficient sequence to allow FBP binding or FBP binding and phosphotyrosine-modulated release of FBP. In another embodiment, the PKM2 polypeptide includes the entire PKM2 sequence. Preferably, the PKM2 polypeptide is present as a tetramer.

In another embodiment, contacting the PKM2 polypeptide and the candidate compound can include: forming a reaction mixture (e.g., a cell-free mixture) containing the PKM2 polypeptide, which can, e.g., be purified or partially purified, and the candidate compound; contacting a cell that expresses the PKM2 polypeptide, e.g., a cancer cell, with the candidate compound; or administering the candidate compound to an animal that expresses the PKM2 polypeptide.

In one specific embodiment, a reaction mixture is formed and includes FBP. Such embodiments are useful in evaluating compounds that activate PKM2 by inhibiting the release of FBP from PKM2.

In another specific embodiment, the reaction mixture excludes FBP. Such embodiments are useful in evaluating compounds which mimic or are agonists of FBP.

In another embodiment, the reaction mixture includes one or more of substrate, cofactor, buffer, and assay or readout reagents.

In another embodiment, a reaction mixture is formed and includes FBP and phosphotyrosine peptide. Such embodiments are useful in evaluating the candidate compound's ability to activate PKM2 by inhibiting the release of FBP from PKM2 in the presence of phosphotyrosine peptide.

In another embodiment, assessing includes the step of evaluating the level of a substrate consumed or a product produced by a reaction catalyzed by PKM2 directly or indirectly. This can include measuring the products of a PKM2 reaction, e.g., ATP or pyruvate, or in a coupled reaction with the presence of lactate dehydrogenase measuring the consumption of NADH and/or the production of lactate. In specific embodiments, the readout of the assessment is made spectroscopically, e.g., colorimetrically or fluorometrically. In another embodiment, the level or rate of consumption/production is compared with a positive control. If the level or rate is equal to or greater than the control, the candidate compound is selected.

In another embodiment, assessing includes using labeled reagents, e.g., a radioisotope-labeled glucose, and scintillation counting to follow the fate of that reagent. Assessing can include measuring PKM2 activity directly by measuring the consumption of ADP or phosphoenolpyruvate, or by measuring the production of ATP or pyruvate. These measurements may be made spectroscopically or by any other method. Production of ATP can also be measured using luminescence by coupling the PKM2 reaction to the luciferase reaction. A change in cellular oxygen consumption can also be measured.

In another embodiment, assessing includes using a coupled enzyme reaction in the presence of a second enzyme that utilizes the product of pyruvate kinase reaction (pyruvate and ATP). In another embodiment, the second enzyme is lactate dehydrogenase which converts pyruvate to lactate in the presence of NADH. In another embodiment, the production of ATP can be measured by a bioluminescence ATP assay.

In another embodiment, the observed ability of the candidate to activate PKM2 is compared with a control or preselected value, and if the observed ability meets a preselected relationship with the control or preselected value, e.g., it meets or exceeds, the candidate compound is selected for further analysis.

Further analysis can include confirming that the candidate compound activates PKM2. In one embodiment, the method further includes performing a second evaluation for the ability to activate PKM2 by the same method. In another embodiment, the method further includes performing a second evaluation for the ability to activate PKM2 by a different method. In certain embodiments, the first method is a cell-free system and the second is a cell-based assay. In alternate embodiments, the first method is a cell-free or cell-based method and the second method is an animal-based method.

In a specific embodiment, the confirmatory assay includes the step of performing a second evaluation for the ability of the candidate compound to activate PKM2 by contacting the candidate compound with a cell and measuring the consumption of oxygen or production of lactate by the cell. In other specific embodiments, a decrease in any of cellular phosphoenolpyruvate, glycerol-phosphate, ribose or deoxyribose, lipid synthesis, or glucose conversion to lipid or nucleic acids or amino acids or protein by the cell can be used to confirm the ability of the candidate compound to activate PKM2. The evaluation could include measuring an increase in pyruvate but this is hard to measure in a cell-based assay. The measurement could also determine alteration in mitochondrial membrane potential, e.g., as measured by fluorescent potentiometric dyes.

In certain embodiments, the confirmatory assay employs an animal-based assay, e.g., one which uses a mouse or rat, and which allows assessment of the ability to activate PKM2 in the animal. In some embodiments, the candidate compound is contacted with a test animal and the conversion of $^{13}$C-labeled glucose to pyruvate or lactate or ribose or other metabolites is followed by MRI in vivo or by mass spectrometry of metabolites from extracted tissues. In certain embodiments, the animal model is evaluated by a method which monitors glucose uptake, e.g., a PET or MRI scan.

In specific embodiments, the candidate compound has one or more properties described herein, e.g., one or more of the following properties: the candidate compound is an allosteric activator; the candidate compound inhibits the release of FBP; the candidate compound is an agonist of FBP, e.g., an agonist which binds with a lower, about the same, or higher affinity than does FBP; the candidate compound inhibits the dissolution of tetrameric PKM2; the candidate compound promotes the assembly of tetrameric PKM2; the candidate compound selectively activates PKM2 over at least one other isoform of PK, e.g., the candidate compound is selective for PKM2 over PKR, PKM1, or PKL; or the candidate compound has an affinity for PKM2 which is greater than its affinity for at least one other isoform of PK, e.g., PKR, PKM1, or PKL. In another embodiment, the method of evaluating the ability of a candidate compound to activate PKM2 further includes evaluating the candidate to determine if it has one of the properties described herein.

In another embodiment, more than one candidate compound is evaluated simultaneously.

In another embodiment, the method of evaluating the ability of a candidate compound to activate PKM2 includes the step memorializing the outcome of an evaluation or assay described herein.

In another aspect, the invention features a method of evaluating a candidate structure for its ability to interact with PKM2. The method can be used to evaluate a candidate structure for use or further investigation for use as an inhibitor or activator of PKM2. The method includes: providing a three dimensional representation of a PKM2 structure, which includes a portion of PKM2 including the FBP binding pocket and preferably Lys433; providing a three dimensional representation of a candidate structure; and evaluating a relationship, e.g., fit, distance, or spatial overlap, between the PKM2 and candidate structures, or between an atom, amino acid, or moiety on the PKM2 structure and an atom or moiety on the candidate structure, thereby evaluating the candidate structure for its ability to interact with PKM2.

The crystal structure of PKM2 complexed with FBP has been reported (see, e.g., Dombrauckas et al., *Biochemistry* 44:9417-29, 2005) and is depicted below.

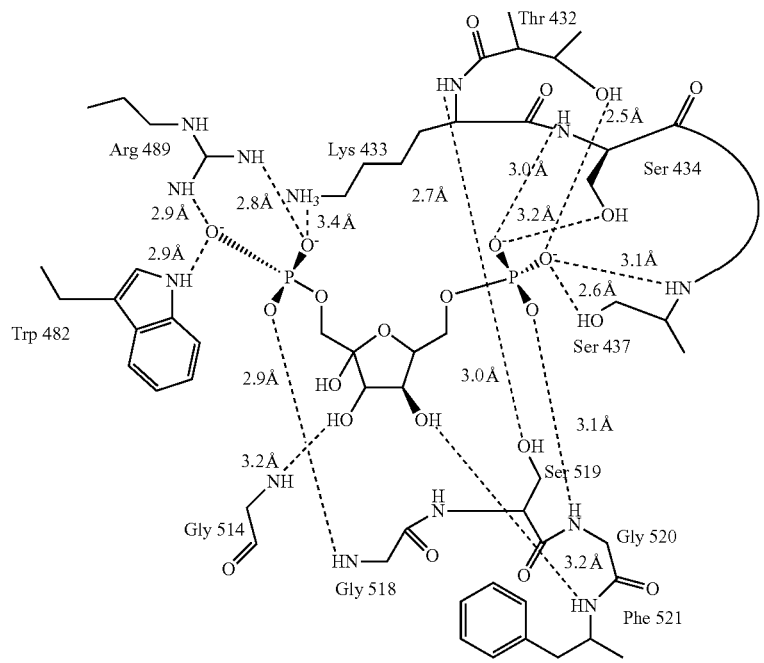

Art-known methods can be used to generate three-dimensional representations of molecules for which the structure is provided or which have been purified or crystallized. Art known methods can be used to produce computer-generated simulations which allow structural comparisons, such as the ability of a candidate structure to "dock" with PKM2.

In another embodiment, a three-dimensional structure can be generated by a modeling program which predicts the three-dimensional structure, for example, from the primary sequence of a protein or peptide. In another embodiment, a three-dimensional structural representation can be generated from a crystal structure.

In another embodiment, the conformation of activator molecules bound to PKM2 can be obtained from NMR measurements of the co-complex of a small molecule activator and PKM2. In some embodiments, the PKM2 structure is provided for a PKM2 bound to FBP. In other embodiments, the PKM2 structure provided is that of PKM2 without bound FBP. In some embodiments, the PKM2 structure provided is bound to a phosphotyrosine-containing polypeptide.

In some embodiments, evaluating includes determining the distance between an atom or moiety of the candidate structure and an atom or moiety of a residue of PKM2, e.g., of a residue in or near, e.g., within 5 angstroms of, the FBP binding pocket, for example, determining if an atom or moiety of the candidate structure and an atom or moiety on the FBP binding pocket make contact or come within a pre-selected distance of one another.

In some embodiments, evaluating includes evaluating the relationship of an atom or moiety of the candidate structure with an atom or moiety of the binding pocket, an atom or moiety of PKM2 within 5 angstroms of the binding pocket, an atom or moiety of FBP residing in the binding pocket, or with an atom or moiety of Lys433.

In some embodiments, evaluating includes determining whether the candidate structure displaces a ligand in the FBP binding pocket or would result in steric hindrance with a bound ligand, e.g., FBP, in the FBP pocket. In other embodiments, evaluating includes determining whether the candidate structure would interfere with occupancy of a ligand in the FBP binding pocket. In other embodiments, evaluating includes determining whether the candidate structure displaces a ligand in the FBP binding pocket or would interfere with release of a ligand in the FBP binding pocket.

In some embodiments, evaluating includes determining whether a shift of amino acid K433 occurs when fitting or docking the PKM2 and candidate structures. In some embodiments, the evaluating includes determining whether one or more interactions occur between the two structures. Exemplary interactions include hydrogen bonding, formation of a salt bridge, hydrophobic interactions, and hydrogen interactions.

In some embodiments, the method further includes making a record of the evaluation, for example, in a tangible medium such as computer memory or on paper. In another embodiment, the record includes an identifier for the candidate structure and a value for a parameter related to the relationship evaluated.

In another embodiment, the method further includes providing a second candidate structure and repeating one or more of the above recited steps on the second candidate structure. In another embodiment, the evaluations for the first and second candidate structures are compared and one is selected for further analysis.

In another embodiment, the method further includes providing instructions to synthesize, purchase, or otherwise obtain a candidate structure evaluated by the method. The identity of a candidate to be synthesized, purchased, or otherwise obtained can be memorialized by creating a record of the identity of the candidate, for example, in a tangible medium such as computer memory or on paper.

In another embodiment, the candidate is tested for its ability to interact with PKM2.

In another aspect, the invention features a pharmaceutical composition of any of the activators described herein.

By "activator" is meant an agent that increases the level of activity of PKM2 from the state of inactive monomeric or dimeric form or maintains or increases the activity of active tetrameric form of PKM2 (e.g., in the presence of an endogenous inhibitor). Increasing activity can include reducing endogenous down-regulation of PKM2 by an endogenous inhibitor (e.g., an endogenous phosphotyrosine peptide or protein). The binding of phosphotyrosine-containing peptide with activated PKM2 results in dissociation of FBP and inactivation of PKM2. Autonomous growth signaling in proliferating cells or stimulation of fat cells by insulin leads to tyrosine phosphorylation cascades. An activator can exert its effect in a number of ways including one or more of the following: an activator can render PKM2 resistant to inhibition by an inhibitor, e.g., an endogenous inhibitor; an activator inhibits release of an activator, more specifically FBP; an activator can bind to PKM2 and prevent an endogenous inhibitor from promoting the release of an endogenous activator, more specifically FBP; or an activator can inhibit the dissolution or promote the reassembly of the subunits which make up PKM2, e.g., an activator can inhibit oxidation of sulfhydryl moieties on such subunits, e.g., inhibit the oxidation of cysteine residues.

An activator can cause PKM2 activity to increase to a level that is greater than PKM2's levels (e.g., basal levels) of activity (e.g., levels seen in the absence of an endogenous or natural activator/ligand, e.g., FBP). For example, the activator may mimic the effect caused by an endogenous or natural ligand or activator (e.g., FBP). The activating effect caused by the agent may be to the same, to a greater, or to a lesser extent than the activating effect caused by an endogenous or natural ligand or activator, but the same type of effect can be caused. Peptides, nucleic acids, and small molecules may be activators. In preferred embodiments, the activator has a molecular weight in the range of 100 or 200 to 10,000, 100 or 200 to 5,000, 100 or 200 to 2,000, or more preferably 100 to 300, 200 to 500, 150 to 500, 200 to 500, 300 to 500, or 150 to 800 Daltons.

Direct activators are activators which interact directly (e.g., bind) by forming a non-covalent bond such as a hydrogen, ionic, electrostatic, or hydrophobic bond, or induce a change in conformation in PKM2, including the tetrameric PKM2 molecule or the monomeric and dimeric molecules, or another activator thereof. In preferred embodiments, the direct activator forms a non-covalent bond with a specific moiety on the PKM2 or endogenous activor (e.g., FBP). Direct activators are preferred.

An expressional activator increases the expression of the PKM2 isoform at the nucleic acid level. This includes activators which induce the expression of PKM2 at the DNA level (e.g., by acting as a co-factor to induce transcription of PKM2) or the RNA level.

An agent can be evaluated to determine if it is an activator by measuring either directly or indirectly the activity of the PKM2 when subjected to the agent. The activity of the agent can be measured, for example, against a control substance. In some instances, direct activation of PKM2 is measured. The activity of PKM2 can be measured, for example, by monitoring the concentration of a substrate or a product directly or indirectly.

All tumor cells exclusively express the embryonic M2 isoform of pyruvate kinase. PKM2 can serve as a target in cancer therapy. PKM2 is also expressed in adipose tissue and activated T-cells and thus activators of PKM2 can be used to treat disorders that are dependent on such cells.

While not wishing to be bound by theory, it is believed that PKM2-dependent cells, e.g., cancer cells, must regulate PKM2, activating it when the cell's need for completion of glycolysis and maximal ATP production is relatively greater and inhibiting it when the cell's need for anabolic processes (growth) is relatively greater. Thus, the endogenous ability to modulate the activity of PKM2 is critically important to the cell. Therapeutic or exogenous modulation of PKM2 by inhibition or activation, e.g., constitutive activation or inhibition, defeats the endogenous modulation or regulation by the cell. Activators can be used to treat disorders related to PKM2 metabolism, e.g., disorders characterized by unwanted cell proliferation, e.g., cancer, obesity, diabetes, atherosclerosis, restenosis, and autoimmune conditions. Selective activators are preferred. Thus, activating PKM2 can mean depriving or compromising the ability of a cell to inactivate PKM2. An activator can reduce the cell's ability to down regulate PKM2 and can, for example, turn regulated PKM2 activity into constitutive PKM2 activity.

By "administering" is meant a method of giving a dosage of a pharmaceutical composition to a patient. The compositions described herein can be administered by a route selected from, e.g., ocular, inhalation, parenteral, dermal, transdermal, buccal, rectal, vaginal, sublingual, perilingual, nasal, topical administration, and oral administration. Parenteral administration includes intravenous, intraperitoneal, subcutaneous, and intramuscular administration. The preferred method of administration can vary depending on various factors, e.g., the components of the composition being administered and the severity of the condition being treated.

By "chemotherapeutic agent" is meant a chemical that may be used to destroy a cancer cell, or to slow, arrest, or reverse the growth of a cancer cell. Chemotherapeutic agents include, e.g., L-asparaginase, bleomycin, busulfan carmustine (BCNU), chlorambucil, cladribine (2-CdA), CPT11 (irinotecan), cyclophosphamide, cytarabine (Ara-C), dacarbazine, daunorubicin, dexamethasone, doxorubicin (adriamycin), etoposide, fludarabine, 5-fluorouracil (5FU), hydroxyurea, idarubicin, ifosfamide, interferon-α (native or recombinant), levamisole, lomustine (CCNU), mechlorethamine (nitrogen mustard), melphalan, mercaptopurine, methotrexate, mitomycin, mitoxantrone, paclitaxel, pentostatin, prednisone, procarbazine, tamoxifen, taxol-related compounds, 6-thiogaunine, topotecan, vinblastine, vincristine, cisplatinum, carboplatinum, oxaliplatinum, or pemetrexed. In another embodiment, the chemotherapeutic agent is not an anti-hypoxic agent.

By "effective amount" is meant the amount of a pharmaceutical composition of the invention required to treat a patient suffering from or susceptible to a disease, such as, e.g., cancer, diabetes, obesity, autoimmune diseases, atherosclerosis, restenosis, and proliferation-dependent diseases. The effective amount of a pharmaceutical composition of the invention used for treatment varies depending upon the manner of administration and the age, body weight, and general health of the subject. Ultimately, the attending prescriber will decide the appropriate amount and dosage regimen. Such an amount is referred to as the "effective amount."

By "immunomodulatory agent" is meant an agent that can elicit or suppress an immune response. Examples of immunomodulatory agents include, e.g., non-steroidal immunophilin-dependent immunosuppressants, e.g., cyclosporine (e.g., Restasis), and steroids, e.g., dexamethasone, rimexolone, fluorometholone, medrysone, and loteprednol etabonate.

By "inhibitor" is meant an agent that measurably slows, stops, decreases, or inactivates the enzymatic activity of PKM2 to a level that is less than the PKM2's basal level of activity. Inhibitors of PKM2 may be small molecules, peptides, or nucleic acids. Decreasing activity can include preventing endogenous up-modulation of PKM2 by an endogenous activator (e.g., an inhibitor can render PKM2 resistant to activation by an activator, e.g., a naturally occurring activator and can, e.g., promote release of an activator, e.g., FBP). In another embodiment, an activator can promote dissolution or inhibit reassembly of the subunits which make up PKM2. In preferred embodiments, the activator has a molecular weight in the range of 100 or 200 to 10,000, 100 or 200 to 5,000, 100 or 200 to 2,000, or more preferably 100 to 300, 200 to 500, 150 to 500, 200 to 500, 300 to 500, or 150 to 800 Daltons.

Direct inhibitors are inhibitors which interact directly (e.g., bind) by, e.g., forming a non-covalent bond such as a hydrogen, ionic, electrostatic, hydrophobic or bond, or induce a change in conformation in PKM2 or a subunit or activator thereof. In preferred embodiments, the direct inhibitor forms a non-covalent bond with a specific moiety on the PKM2 or endogenous activator (e.g., FBP). Direct inhibitors are preferred. A direct inhibitor can be one that exerts its effect at the protein level, or one that exerts its effect at the nucleic acid level. An example of the former is a compound that interacts with one or both of PKM2 and FBP to promote release of FBP from PKM2. An example of the latter is a nucleic acid-based drug, e.g., an siRNA or an antisense molecule, which targets a subunit of a PKM2.

An agent can be evaluated to determine if it is an inhibitor by measuring either directly or indirectly the activity of PKM2 when subjected to the agent. The activity of the agent can be measured, for example, against a control substance. In some instances, the activity measured of the agent is for inhibition of PKM2. The activity of PKM2 can be measured, for example, by monitoring the concentration of a substrate such as lactate or NADH.

By "modulator" is meant an agent that modulates (e.g., activates or inhibits) the activity of pyruvate kinase (e.g., PKM2). For example, the modulator may be, e.g., a peptide that inhibits the activity of pyruvate kinase. Alternatively, a modulator may be, e.g., a nucleic acid (e.g., siRNA) or small molecule. Modulators may be useful in the treatment of, e.g., cancer, diabetes, obesity, autoimmune diseases, neurological diseases (e.g., Parkinson's disease and Alzheimer's disease), proliferation-dependent diseases, and other diseases associated with the function of pyruvate kinase.

By "patient" is meant any animal, e.g., mammal (e.g., a human).

By "pharmaceutical composition" is meant any composition that contains at least one therapeutically or biologically active agent and is suitable for administration to a patient. For the purposes of this invention, pharmaceutical compositions suitable for delivering a therapeutic can include, e.g., eye drops, tablets, gelcaps, capsules, pills, powders, granulates, suspensions, emulsions, solutions, gels, hydrogels, oral gels, pastes, ointments, creams, plasters, drenches, delivery devices, suppositories, enemas, injectables, implants, sprays, or aerosols. Any of these formulations can be prepared by well-known and accepted methods of art. See, for example, *Remington: The Science and Practice of Pharmacy* (21$^{st}$ ed.), ed. A. R. Gennaro, Lippincott Williams & Wilkins, 2005, and *Encyclopedia of Pharmaceutical Technology*, ed. J. Swarbrick, Informa Healthcare, 2006, each of which is hereby incorporated by reference.

Agents useful in the pharmaceutical compositions of the invention may include those described herein in any of their pharmaceutically acceptable forms, including isomers such as diastereomers and enantiomers, salts, solvates, prodrugs, and polymorphs, thereof, as well as racemic mixtures of the agents described herein.

By "prodrug" is meant a molecule that, upon metabolism in the body of a subject, is chemically converted to another molecule serving a therapeutic or other pharmaceutical purpose (e.g., a drug molecule containing a carboxylic acid contains an amide or an ester bond in its prodrug form, which is cleaved upon metabolism).

By "selective" is meant at least 20%, 50%, 75%, 2-fold, 3-fold, 4-fold, 5-fold, 6-fold, or 10-fold greater inhibition of a PKM2 over a second kinase, e.g., a second pyruvate kinase, e.g., a different isoform. Thus, in some embodiments, the agent is selective for PKM2 over another isoform. For example, an agent is selective for PKM2 relative to PKM1. Selective regulation, e.g., inhibition or activation, or selective modulation, are used interchangeably with specific regulation or specific modulation.

By "substantially identical" is meant a polypeptide or peptide exhibiting at least 60%, 65%, 70%, 75%, 80%, 85%, 90%, 95%, 98%, 99%, or even 100% identity to a reference amino acid or nucleic acid sequence over contiguous residues.

Sequence identity is typically measured using a sequence analysis program (e.g., BLAST 2; Tatusova et al., FEMS Microbiol Lett. 174:247-250, 1999) with the default parameters specified therein. Conservative substitutions typically include substitutions within the following groups: glycine, alanine, valine, isoleucine, leucine; aspartic acid, glutamic acid, asparagine, glutamine; serine, threonine; lysine, arginine; and phenylalanine and tyrosine.

By "therapeutic agent" is meant any agent that produces a preventative, healing, curative, stabilizing, or ameliorative effect.

By "treating" is meant administering a pharmaceutical composition for prophylactic and/or therapeutic purposes. Prophylactic treatment may be administered, for example, to a subject who is not yet ill, but who is susceptible to, or otherwise at risk of, a particular disorder, e.g., cancer. Therapeutic treatment may be administered, for example, to a subject already suffering from a disorder in order to improve or stabilize the subject's condition. Thus, in the claims and embodiments described herein, treating is the administration to a subject either for therapeutic or prophylactic purposes. In some instances, as compared with an equivalent untreated control, treatment may ameliorate a disorder or a symptom thereof by, e.g., 5%, 10%, 20%, 30%, 40%, 50%, 60%, 70%, 80%, 90%, 95%, or 100% as measured by any standard technique. In some instances, treating can result in the inhibition of a disease, the healing of an existing disease, and the amelioration of a disease.

As used herein, the terms "inhibit" or "prevent" include both complete and partial inhibition or prevention. An inhibitor may completely or partially inhibit. As used herein, the term "activate" can refer to different levels of activation.

Other features and advantages of the invention will be apparent from the following detailed description, the drawings, and the claims.

BRIEF DESCRIPTION OF THE DRAWINGS

FIG. 1a shows a schematic of the proteomic screen for phosphotyrosine binding proteins using SILAC and peptide library affinity matrices. FIG. 1b shows the screening results using commercially available software with the SILAC ratios (heavy:light) for the proteins identified by LC-MS/MS. Background proteins yielded ~1:1 SILAC ratios. Known phosphotyrosine-binding proteins yielded >3:1 SILAC ratios. Pyruvate kinase yielded a ≥15:1 SILAC ratio. FIG. 1c shows a silver stain of proteins from HeLa cell lysates that bound to the pTyr versus Tyr peptide library columns. Differentially stained proteins identified by LC-MS/MS are indicated. FIG. 1d shows an immunoblot of proteins from HeLa cell lysates that bound to the pTyr versus Tyr peptide library columns. Eluates from the columns were immunoblotted with antibodies for pyruvate kinase, p85 as a positive control, and GAPDH as a negative control.

FIG. 2a shows an immunoblot illustrating the pyruvate kinase isoform specificity of pTyr binding. The M1, M2, M2KE, and L flag-tagged pyruvate kinase isoforms were stably expressed in H1299 cells, and lysates were flowed over the pTyr (pY) and Tyr (Y) peptide library columns. The flow-throughs and eluates from the columns were immunoblotted with flag antibody. M2KE stands for the K433E point mutant of PKM2. FIG. 2b shows a Coomassie-stained SDS-PAGE gel of PKM2 bound to the pTyr peptide library column after incubation with increasing amounts of FBP. Recombinant PKM2 was incubated with increasing concentrations of FBP, as indicated, prior to being flowed over and eluted from the pTyr peptide library affinity matrix with sodium phenylphosphate.

FIG. 4a shows the representative composite omit 2Fo-Fc electron density map for FBP contoured to 1.2 sigma. FIG. 4b is a close-up of the allosteric pocket of PKM2 showing an overlay of the FBP-bound structure and the apo structure. The flexible FBP activation loop, including residues W515-G520, is structured in the FBP-bound form of PKM2, but not in the apo-form of PKM2. FIG. 4c shows the surface electrostatic potential of the FBP binding pocket in the same orientation as in FIG. 4b. The bound FBP is completely enclosed by the protein except for the P1 phosphate group. FIG. 4d shows a schematic of the experimental procedure to test the effect of pTyr peptide binding on FBP release from PKM2. FIG. 4e shows $^{14}$C scintillation counts retained on recombinant PKM2 after exposure to P-M2tide versus NP-M2tide. Bars denote s.e.m. (n=3).

FIG. 5 shows the sequence of the P-M2tide that was obtained by traditional peptide library screening. Both the P-M2tide and the unphosphorylated control peptide, NP-M2tide, were synthesized.

FIG. 6a shows a comparison of pyruvate kinase activity in the presence of FBP, P-M2tide (P), and NP-M2tide (NP). FIG. 6b shows a comparison of pyruvate kinase activity in the presence of various pTyr peptides. Eight of the phosphopeptides tested included previously mapped pTyr sites on the metabolic proteins indicated. Four of the phosphopeptides tested were designed after known tyrosine kinase motifs. Since all of the peptides were dissolved in DMSO, DMSO was used as a negative control. FIG. 6c shows a comparison of pyruvate kinase activity in lysates from 293, A549, and H1299 cells with (pv) and without (−) pervanadate stimulation. FIG. 6d shows a comparison of pyruvate kinase activity in lysates from 293 cells that were mock-transfected (mock) or transiently transfected with constitutively-active Src kinase (CA-Src). FIG. 6e shows a comparison of pyruvate kinase activity in lysates from A549 cells that were serum-starved overnight with and without (starve) fifteen minutes of 20 nM IGF-stimulation (IGF). FIG. 6f shows an immunoblot of lysates from H1299 cells stably expressing shRNA constructs and rescue constructs. Total cell extracts were immunoblotted with antibodies for pyruvate kinase (which recognizes both the M1 and M2 isoforms), flag, and GAPDH. Note that PKL was not recognized by the pyruvate kinase antibody. FIG. 6g shows a comparison of pyruvate kinase activity in lysates from H1299 cells expressing knockdown shRNA and flag-PKM1, PKM2, PKM2KE, and PKL with and without pervanadate stimulation (pv). Bars denote s.e.m. (n=3) in FIGS. 6a, 6b, 6c, 6d, 6e, and 6g.

In FIGS. 7a and 7b, (cl pLHCX) represents cells with empty rescue vector and control shRNA; (kd pLHCX) represents cells with empty rescue vector and knockdown shRNA; (kd mM2) represents cells with flag-mouse PKM2 rescue and knockdown shRNA; (kd mKE) represents cells with flag-mouse PKM2 KE point mutant rescue and knockdown shRNA. FIG. 7a shows the glycolytic rates of the knockdown and rescue H1299 cells. FIG. 7b shows proliferation curves of the knockdown and rescue H1299 cells. Bars denote s.e.m. (n=3) in FIGS. 7a and 7b.

DETAILED DESCRIPTION

Figure 1:
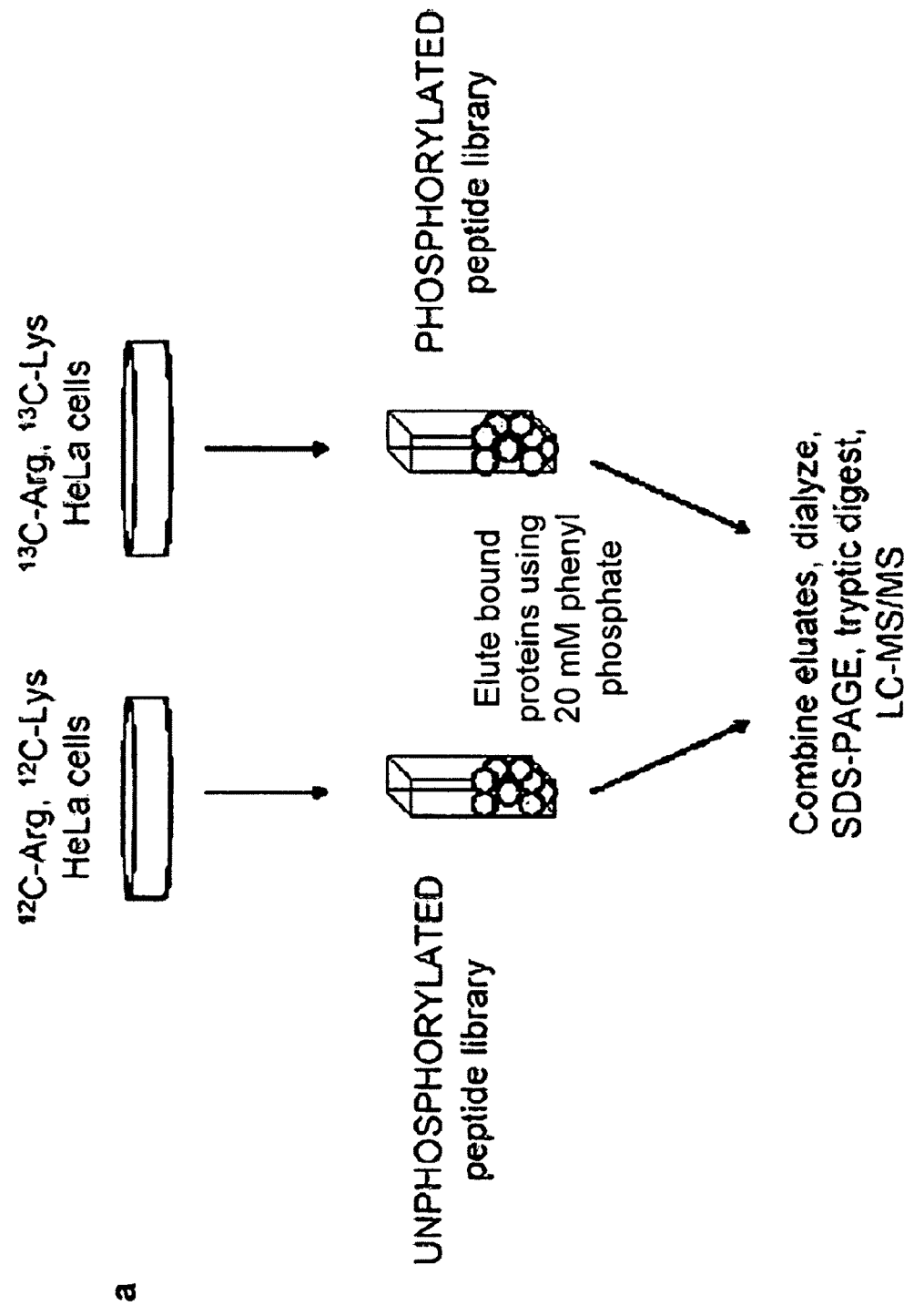
FIG. 1 shows a proteomic screen identifying pyruvate kinase as a novel pTyr binding protein.
Figure 1:
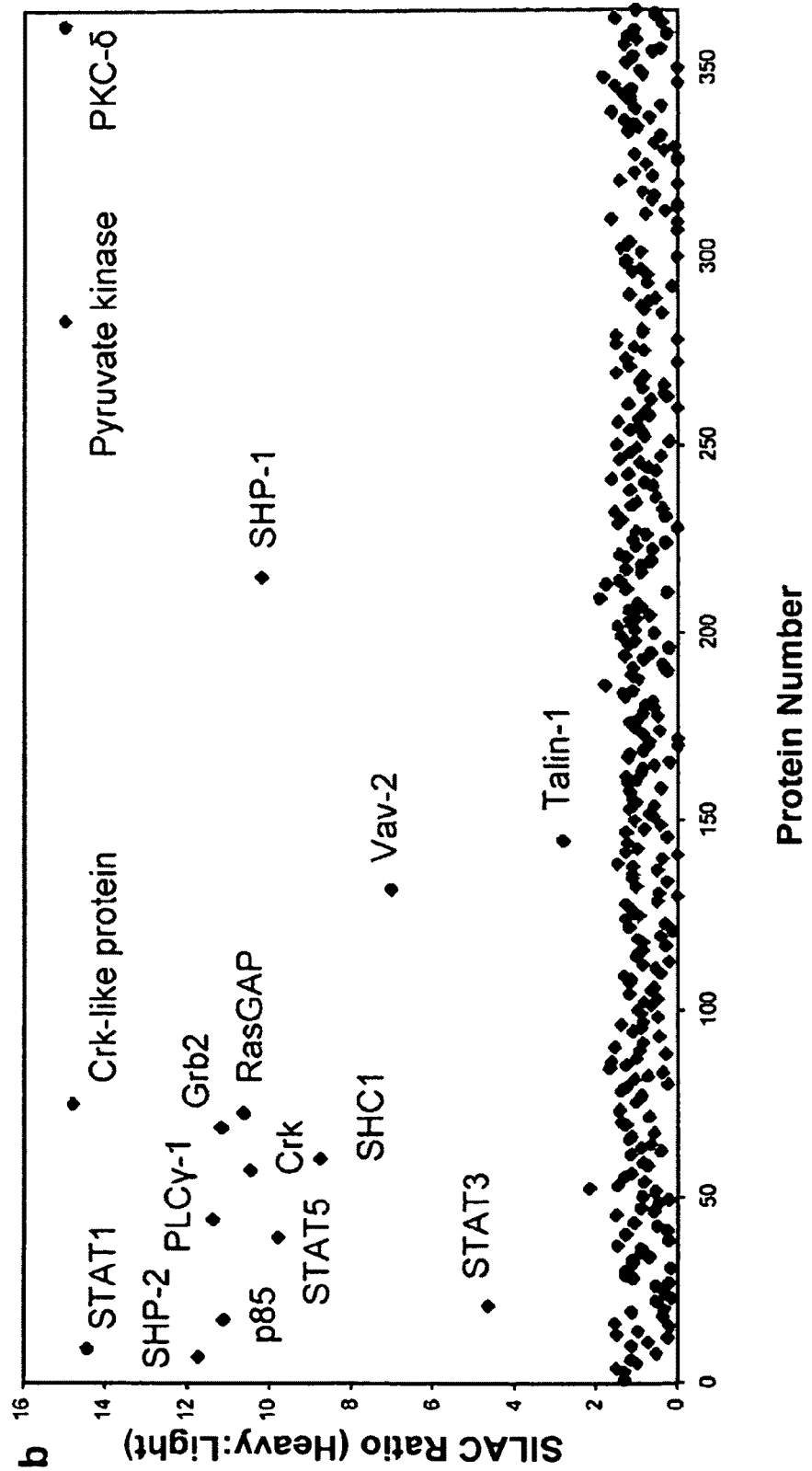
Figure 1:
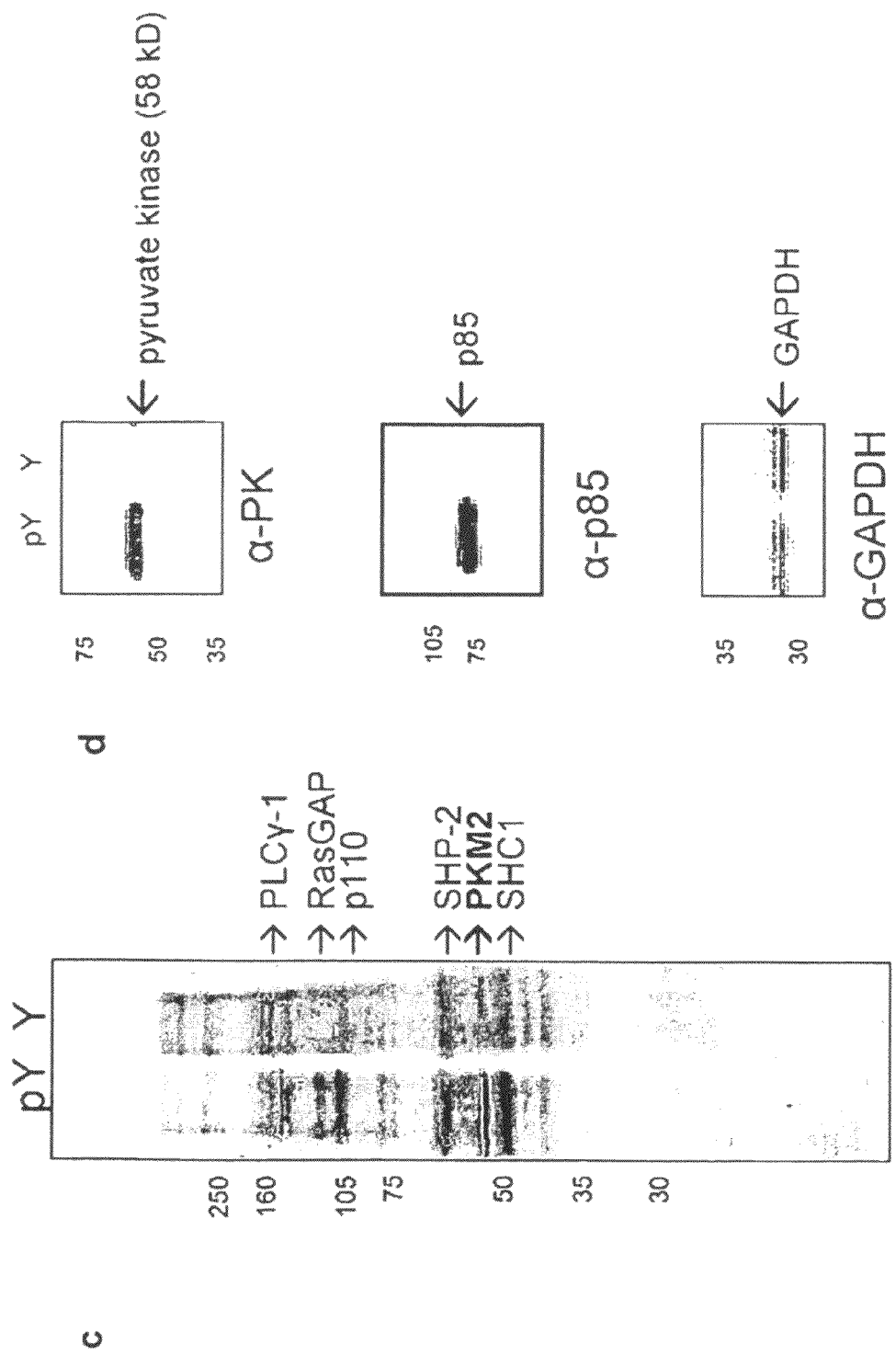

The invention described herein features methods, compositions, and kits that use of activators of PKM2 for the treatment, prevention, or amelioration of diseases related to pyruvate kinase function, including, e.g., cancer, diabetes, atherosclerosis, restenosis, obesity, autoimmune diseases, and proliferative diseases.

Proliferating cells and fat cells express PKM2 specifically; thus, the activators and methods used herein are particularly useful for treating disorders having unwanted activity or numbers of such cells. The invention provides optimized and selective treatments of diseases associated with PKM2 function including, e.g., cancer, atherosclerosis, restenosis, obesity, autoimmune conditions, proliferation-dependent diseases, and other diseases associated with the function of PKM2.

PKM2 traps its allosteric activator, FBP, in a binding pocket bracketed by Lys433 and that collision with a Tyr-phosphorylated polypeptide is required for release of FBP from PKM2 and subsequent inhibition of enzymatic activity.

Constitutive activation of pyruvate kinase activities in cancer cells support tumorigenesis, as evidenced by replacing PKM2 activity with PKM1 in cancer cells. Note that PKM1 is constitutively active and does not bind to FBP. Together, these results show that an on-and-off switch of glycolysis by allosterically modulating the activity of PKM2 with FBP and phosphotyrosine-containing peptide(s)/proteins is required for growth of proliferating cells (e.g., cancer cells). Constitutive activation of PKM2 presents an approach to reprogram glycolysis/metabolism of proliferating cells and ameliorating diseases associated or dependent on modulation of cell glycolysis by PKM2

Diagnosis and Treatment of Diseases Associated with PKM2 Function

Diseases treated by the methods, compositions, and kits described herein may be caused by or associated with, e.g., the function PKM2. These diseases may include, e.g., cancer, obesity, diabetes, atherosclerosis, restenosis, autoimmune diseases, and proliferation-dependent diseases.

Cancer

Activators of PKM2 described herein may be used in the treatment of, e.g., cancer. Cancers include, without limitation, leukemias (e.g., acute leukemia, acute lymphocytic leukemia, acute lymphocytic leukemia, acute myelocytic leukemia, acute myeloblastic leukemia, acute promyelocytic leukemia, acute myelomonocytic leukemia, acute monocytic leukemia, acute erythroleukemia, chronic leukemia, chronic myelocytic leukemia, chronic lymphocytic leukemia), polycythemia vera, lymphoma (e.g., Hodgkin's disease or non-Hodgkin's disease), Waldenstrom's macroglobulinemia, multiple myeloma, heavy chain disease, and solid tumors such as sarcomas and carcinomas (e.g., fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, colon carcinoma, pancreatic cancer, breast cancer, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilm's tumor, cervical cancer, uterine cancer, testicular cancer, lung carcinoma, small cell lung carcinoma, bladder carcinoma, epithelial carcinoma, glioma, astrocytoma, medulloblastoma, craniopharyngioma, ependymoma, pinealoma, hemangioblastoma, acoustic neuroma, oligodendroglioma, schwannoma, meningioma, melanoma, neuroblastoma, and retinoblastoma).

Diabetes and Obesity

Adipose tissue expresses PKM2. Thus, the methods, compositions, and kits of the invention described herein may be useful in the treatment of obesity. Additionally, activators of PKM2, described herein, may be useful in the treatment of type II diabetes, as the activation of PKM2 may allow for decreased lipid production and increased oxidative phosphorylation in adipose tissue. This effect should decrease adiposity, which is known to contribute to type 2 diabetes.

Autoimmune Diseases and Proliferative Diseases

Activators of PKM2, described herein, may be used to treat, e.g., autoimmune diseases or proliferative diseases. Autoimmune disorders include, e.g., type I diabetes, Crohn's disease, multiple sclerosis, arthritis, rheumatoid arthritis, systemic lupus erythematosus, autoimmune (Hashimoto's) thyroiditis, autoimmune liver diseases (e.g., hepatitis and primary biliary cirrhosis), hyperthyroidism (e.g., Graves' disease and thyrotoxicosis), insulin-resistant diabetes, autoimmune adrenal insufficiency (e.g., Addison's disease), autoimmune oophoritis, autoimmune orchitis, autoimmune hemolytic anemia, paroxysmal cold hemoglobinuria, Behcet's disease, autoimmune thrombocytopenia, autoimmune neutropenia, pernicious anemia, pure red cell anemia, autoimmune coagulopathies, myasthenia gravis, experimental allergic encephalomyelitis, autoimmune polyneuritis, pemphigus and other bullous diseases, rheumatic carditis, Goodpasture's syndrome, postcardiotomy syndrome, Sjogren's syndrome, polymyositis, dermatomyositis, and scleroderma. Autoimmune disorders are described in U.S. Pat. Nos. 5,891,435 and 6,773,705, hereby incorporated by reference.

Proliferative diseases include, e.g., cancer (e.g., benign and malignant), benign prostatic hyperplasia, psoriasis, abnormal keratinization, lymphoproliferative disorders (e.g., a disorder in which there is abnormal proliferation of cells of the lymphatic system), chronic rheumatoid arthritis, arteriosclerosis, restenosis, and diabetic retinopathy. Proliferative diseases are described in U.S. Pat. Nos. 5,639,600 and 7,087,648, hereby incorporated by reference.

Therapy

Therapy according to the methods described herein may be performed alone or in conjunction with another therapy, and may be provided at home, the doctor's office, a clinic, a hospital's outpatient department, or a hospital. Treatment generally begins at a hospital so that the doctor can observe the therapy's effects closely and make any adjustments that are needed. The duration of the therapy depends on the age and condition of the patient, the severity of the patient's disease, and how the patient responds to the treatment.

Activators

Activators may be, e.g., peptides, nucleic acids, or small molecules. Peptides useful as activators in the methods, compositions, and kits described herein, can include modifications, e.g., in vivo or in vitro chemical derivatization of polypeptides (e.g., acetylation or carboxylation). Also included are modifications of glycosylation, e.g., those made by modifying the glycosylation patterns of a polypeptide during its synthesis and processing, or in further processing steps, e.g., by exposing the peptide to enzymes that affect glycosylation derived from cells that normally provide such processing, e.g., mammalian glycosylation enzymes. Also encompassed are versions of the same primary amino acid sequence that have phosphorylated amino acid residues, e.g., phosphotyrosine, phosphoserine, or phosphothreonine.

Peptides useful as activators may be synthetic or purified from natural sources. The peptides may be available commercially or may be produced in recombinant or non-recombinant cells lines. Characterization of isolated peptidic activators may be accomplished using, e.g., solution assays, gel assays (e.g., SDS-PAGE), membrane-bound methods, antibodies, enzyme-linked immuno-sorbent assays (ELISA), or liquid-chromatography electron-spray ionization mass spectrometry (LCMS).

Exemplary activators of PKM2 can be selected from the following candidates: 1,6-fructose-bis-phosphate, dithiothreitol, 2,5-anhydro-D-mannitol 1,6 bis-phosphate, AMP, phosphoenolpyruvate, and the following structures below.

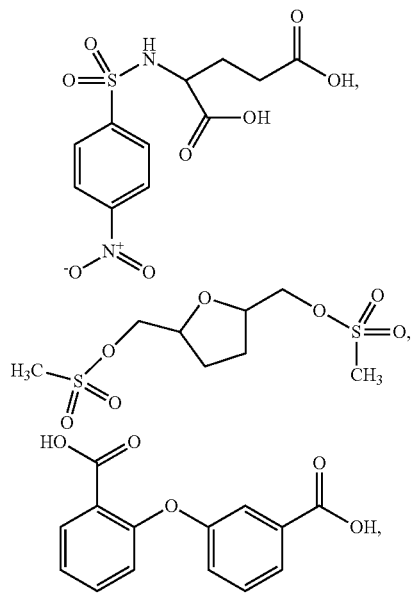

-continued

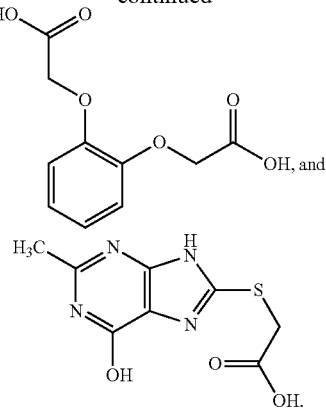

Activators are useful in the treatment of, e.g., cancer, diabetes, obesity, autoimmune diseases, atherosclerosis, restenosis, proliferation diseases, and other diseases associated with the function of PKM2.

Therapeutic Agents

If desired, additional therapeutic regimens may be provided along with the activators described herein. In some embodiments, the additional therapeutic agent is an inhibitor of cystine oxidation. In some embodiments, the additional therapeutic agent is an inhibitor of glutamine metabolism. For example, therapeutic agents may be administered with the activators of PKM2 activity described herein at concentrations known to be effective for such therapeutic agents. Particularly useful agents include, e.g., chemotherapeutic agents, immunomodulatory agents, metabolic modulators, anti-diabetic drugs, e.g., an oral anti-diabetes drug, e.g., metformin, or insulin or insulin analogs or derivatives, as discussed elsewhere herein.

Chemotherapeutic Agents

Any suitable chemotherapeutic agent may be administered. Chemotherapeutic agents suitable for the composition described herein include, e.g., asparaginase, bleomycin, busulfan carmustine (BCNU), chlorambucil, cladribine (2-CdA), CPT11, cyclophosphamide, cytarabine (Ara-C), dacarbazine, daunorubicin, dexamethasone, doxorubicin (adriamycin), etoposide, fludarabine, 5-fluorouracil (5FU), hydroxyurea, idarubicin, ifosfamide, interferon-α (native or recombinant), levamisole, lomustine (CCNU), mechlorethamine (nitrogen mustard), melphalan, mercaptopurine, methotrexate, mitomycin, mitoxantrone, paclitaxel, pentostatin, prednisone, procarbazine, tamoxifen, taxol-related compounds, 6-thioguanine, topotecan, vinblastine, and vincristine. Exemplary agents include cisplatinum, carboplatinum, oxaliplatinum, and pemetrexed. Exemplary chemotherapeutic agents are listed in, e.g., U.S. Pat. Nos. 6,864,275 and 6,984,654, hereby incorporated by reference. Hormonal therapy can be administered and may include, e.g., anti-estrogens and anti-androgens. Anti-estrogen therapy can be used in the treatment of breast cancer. Anti-androgen therapy can be used in the treatment of prostate cancer.

Immunomodulatory Agents

Immunomodulatory agents are agents that can elicit or suppress an immune response. Examples of useful immunomodulatory agents include non-steroidal immunophilin-dependent immunosuppressants, e.g., ascomycin, cyclosporine (e.g., Restasis), everolimus, pimecrolimus, rapamycin, and tacrolimus. Also included are steroids, e.g., beclomethasone, budesonide, dexamethasone, fluorometholone, fluticasone, hydrocortisone, loteprednol etabonate, medrysone, rimexolone, and triamcinolone. Exemplary steroids are listed in, e.g., U.S. Pat. Nos. 5,837,698 and 6,909,007, hereby incorporated by reference.

Additional Therapeutic Regimens

If more than one agent is employed, therapeutic agents may be delivered separately or may be admixed into a single formulation. When agents are present in different pharmaceutical compositions, different routes of administration may be employed. Routes of administration include, e.g., ocular, inhalation, parenteral, dermal, transdermal, buccal, rectal, sublingual, perilingual, nasal, topical administration, or oral administration. Parenteral administration includes intravenous, intraperitoneal, subcutaneous, and intramuscular administration.

The therapeutic agents described herein may be admixed with additional active or inert ingredients, e.g., in conventional pharmaceutically acceptable carriers. A pharmaceutical carrier can be any compatible, non-toxic substance suitable for the administration of the compositions of the present invention to a patient. Pharmaceutically acceptable carriers include, for example, water, saline, buffers and other compounds, described, for example, in the Merck Index, Merck & Co., Rahway, N.J. Slow-release formulations or a slow-release apparatus may be also be used for continuous administration.

In addition to the administration of therapeutic agents, the additional therapeutic regimen may involve other therapies, including modification to the lifestyle of the subject being treated.

Formulation of Pharmaceutical Compositions

The administration of the compositions described herein may be by any suitable means that results in a concentration of the activator and, optionally, therapeutic agent, that is effective in treating the disease associated with PKM2 function. The composition may be contained in any appropriate amount in any suitable carrier substance. The composition may be provided in a dosage form that is suitable for the oral, parenteral (e.g., intravenous or intramuscular), rectal, cutaneous, nasal, vaginal, inhalant, skin (e.g., a patch), ocular, or intracranial administration route. Thus, the composition may be in the form of, e.g., tablets, capsules, pills, powders, granulates, suspensions, emulsions, solutions, gels including hydrogels, pastes, ointments, creams, plasters, drenches, osmotic delivery devices, suppositories, enemas, injectables, implants, sprays, or aerosols. The pharmaceutical compositions may be formulated according to conventional pharmaceutical practice (see, e.g., Remington: *The Science and Practice of Pharmacy,* 20th edition, 2000, ed. A. R. Gennaro, Lippincott Williams & Wilkins, Philadelphia, and *Encyclopedia of Pharmaceutical Technology*, eds. J. Swarbrick and J. C. Boylan, 1988-1999, Marcel Dekker, New York).

Pharmaceutical compositions according to the invention may be formulated to release the active agent immediately upon administration or at any predetermined time or time period after administration. The latter types of compositions are generally known as controlled-release formulations, which include (i) formulations that create substantially constant concentrations of the agent(s) of the invention within the body over an extended period of time; (ii) formulations that after a predetermined lag time create substantially constant concentrations of the agents of the invention within the body over an extended period of time; (iii) formulations that sustain the agent(s) action during a predetermined time period by maintaining a relatively constant, effective level of the agent(s) in the body with concomitant minimization of undesirable side effects associated with fluctuations in the plasma level of the agent(s) (sawtooth kinetic pattern); (iv) formulations that localize action of agent(s), e.g., spatial placement of a controlled release composition adjacent to or in the diseased tissue or organ; (v) formulations that achieve convenience of dosing, e.g., administering the composition once per week or once every two weeks; and (vi) formulations that target the action of the agent(s) by using carriers or chemical derivatives to deliver the combination to a particular target cell type. Administration of the combination in the form of a controlled-release formulation is especially preferred for compounds having a narrow absorption window in the gastrointestinal tract or a relatively short biological half-life.

Any of a number of strategies can be pursued in order to obtain controlled release in which the rate of release outweighs the rate of metabolism of the composition in question. In one example, controlled release is obtained by appropriate selection of various formulation parameters and ingredients, including, e.g., various types of controlled release compositions and coatings. Thus, the combination is formulated with appropriate excipients into a pharmaceutical composition that, upon administration, releases the combination in a controlled manner. Examples include single or multiple unit tablet or capsule compositions, oil solutions, suspensions, emulsions, microcapsules, molecular complexes, microspheres, nanoparticles, patches, and liposomes.

Formulations for parenteral administration may, for example, contain excipients, sterile water, or saline, polyalkylene glycols such as polyethylene glycol, oils of vegetable origin, or hydrogenated naphthalenes. Biocompatible, biodegradable lactide polymer, lactide/glycolide copolymer, or polyoxyethylene-polyoxypropylene copolymers may be used to control the release of the compounds. Nanoparticulate formulations (e.g., biodegradable nanoparticles, solid lipid nanoparticles, and liposomes) may be used to control the biodistribution of the compounds. Other potentially useful parenteral delivery systems include ethylene-vinyl acetate copolymer particles, osmotic pumps, implantable infusion systems, and liposomes.

Formulations for inhalation may contain excipients or may be aqueous solutions containing, for example, polyoxyethylene-9-lauryl ether, glycolate and deoxycholate, or may be oily solutions for administration in the form of nasal drops, or as a gel. The concentration of the compound in the formulation will vary depending upon a number of factors, including the dosage of the drug to be administered, and the route of administration.

Formulations for oral use include tablets containing the active ingredient(s) in a mixture with non-toxic pharmaceutically acceptable excipients. These excipients may be, for example, inert diluents or fillers (e.g., sucrose and sorbitol), lubricating agents, glidants, and anti-adhesives (e.g., magnesium stearate, zinc stearate, stearic acid, silicas, hydrogenated vegetable oils, or talc). Formulations for oral use may also be provided in unit dosage form as chewable tablets, tablets, caplets, or capsules (e.g., as hard gelatin capsules wherein the active ingredient is mixed with an inert solid diluent or as soft gelatin capsules wherein the active ingredient is mixed with water or an oil medium).

The composition may be optionally administered as a pharmaceutically acceptable salt, such as, e.g., a non-toxic acid addition salt or metal complex that is commonly used in the pharmaceutical industry. Examples of acid addition salts include, e.g., organic acids (e.g., acetic, lactic, pamoic, maleic, citric, malic, ascorbic, succinic, benzoic, palmitic, suberic, salicylic, tartaric, methanesulfonic, toluenesulfonic, or trifluoroacetic acids), polymeric acids (e.g., tannic acid or carboxymethyl cellulose), and inorganic acids (e.g., hydrochloric acid, hydrobromic acid, sulfuric acid, or phosphoric acid). Metal complexes include, e.g., zinc and iron complexes.

The formulations can be administered to human subjects in therapeutically effective amounts. Typical dose ranges are from about 0.01 µg/kg to about 2 mg/kg of body weight per day. The preferred dosage of drug to be administered is likely to depend on such variables as the type and extent of the disorder, the overall health status of the particular subject, the specific compound being administered, the excipients used to formulate the compound, and its route of administration. Standard clinical trials maybe used to optimize the dose and dosing frequency for any particular composition.

Dosages

The pharmaceutical compositions described herein may be administered once, twice, three times, four times, or five times each day, or in other quantities and frequencies. Alternatively, the pharmaceutical composition may be administered once per week, twice per week, three times per week, four times per week, five times per week, or six times per week. Therapy with the composition described herein can continue until the disease or disorder has been ameliorated. The duration of therapy can be, e.g., one week to one month; alternatively, the pharmaceutical composition can be administered for a shorter or a longer duration. Continuous daily dosing with the compositions used in the methods and kits described herein may not be required. A therapeutic regimen may require cycles, during which time a composition is not administered, or therapy may be provided on an as-needed basis.

Appropriate dosages of compounds used in the methods described herein depend on several factors, including the administration method, the severity of the disease, and the age, weight, and health of the patient to be treated. Additionally, pharmacogenomic information (e.g., the effect of genotype on the pharmacokinetic, pharmacodynamic, or efficacy profile of a therapeutic) about a particular patient may affect the dosage used.

EXAMPLES

It is shown herein that the M2 (fetal) isoform of human pyruvate kinase (PKM2) binds selectively to Tyr-phosphorylated peptides. A crystal structure of recombinant PKM2 revealed that the enzyme retained bacterial fructose-1,6-bisphosphate (FBP) in the allosteric regulatory pocket. A phosphoTyr peptide optimized for binding to PKM2 stimulated release of FBP and inhibition of enzymatic activity. Lys433 in the lip of the FBP binding pocket of PKM2 was found to be critical for phosphoTyr peptide binding but not for FBP binding. The M1 and L isoforms of pyruvate kinase have Glu and Thr residues respectively at positions analogous to Lys433 and fail to bind phosphoTyr peptides. Importantly, a variety of stimuli that activate protein-Tyr kinases in cells in culture inhibited the activity of endogenous PKM2, but did not affect the activities of PKM1, PKL or the Lys433 to Glu mutant of PKM2. Finally, replacement of endogenous PKM2 with the Lys433 to Glu mutant impaired cell growth. These results indicate a novel mechanism by which growth factor receptor protein-Tyr kinases regulate PKM2 that involves release of trapped FBP due to collision with Tyr-phosphorylated proteins. This mechanism appears to be important for the growth of certain cancer cells (see, e.g., Christofk et al., *Nature* 452: 181-186, 2008, and Examples 1-6, below).

It also shown herein that a single switch in a splice isoform of the glycolytic enzyme, pyruvate kinase, is necessary for the shift in cellular metabolism to aerobic glycolysis and that this promotes tumorigenesis. Tumor cells have been shown to exclusively express the embryonic M2 isoform of pyruvate kinase. Short hairpin RNA was used to knockdown pyruvate kinase M2 expression in cancer cell lines and replace it with pyruvate kinase M1. Switching pyruvate kinase expression to the M1 (adult) isoform leads to reversal of the Warburg effect as judged by reduced lactate production and increased oxygen consumption, and this correlates with a reduced ability to form tumors in nude mouse xenografts. These results demonstrate that M2 expression is necessary for aerobic glycolysis and that this metabolic phenotype provides a selective growth advantage for tumor cells in vivo (see, e.g., Christofk et al., Nature 452: 230-233, 2008, and Example 7, below).

The following examples are put forth so as to provide those of ordinary skill in the art with a complete disclosure and description of how the methods, compositions, and kits claimed herein are performed, made, and evaluated, and are intended to be purely exemplary of the invention and are not intended to limit the scope of what the inventors regard as their invention.

Example 1

Proteomic Screen Identifies Pyruvate Kinase as a Novel Phosphotyrosine Binding Protein A phosphotyrosine peptide library (pY) and its unphosphorylated counterpart (Y) were constructed as follows: pY=biotinZ-Z-Gly-Gly-Gly-X-X-X-X-X-pTyr-X-X-X-X-X-Gly-Gly and Y=biotin-Z-Z-GlyGly-Gly-X-X-X-X-X-Tyr-X-X-X-X-X-Gly-Gly, where pTyr is phosphotyrosine, Z indicates aminohexanoic acid, and X denotes all amino acids except cysteine (Tufts Core Facility). Streptavidin beads (Amersham Biosciences) were incubated with a five-fold molar excess of each biotinylated library in TBST (50 mM Tris (pH 7.5), 150 mM NaCl, and 0.1% Tween) for 1 hour at 4° C. Peptide-conjugated beads were packed onto disposable 1-ml chromatography columns (Bio-Rad Laboratories) (250 pL beads/column) and were rapidly washed five times with TBST.

To identify novel phosphoTyr binding proteins from cell lysates, proteomic screening was used (FIG. 1a). Using SILAC (stable isotope labeling of amino acids in cell culture; Ong and Mann, Methods Mol. Biol. 359:37-52, 2007), lysates from HeLa cells grown in either heavy isotopic $^{13}$C-arginine and $^{13}$C-lysine or normal isotopic $^{12}$C-arginine and $^{12}$C-lysine were prepared. As described in Ong and Mann, HeLa cells were grown in DMEM media that lacked arginine and lysine (Gibco) and dialyzed in FBS. The media was supplemented with heavy $^{13}$C$_6$-L-arginine and $^{13}$C$_6$-L-lysine (Cambridge Isotope Laboratories) or with $^{12}$C$_6$-L-arginine and $^{12}$C$_6$-L-lysine (Sigma). Cells were passaged five timed in "heavy" or "light" SILAC media to ensure complete labeling. Mammalian cells were lysed in buffer containing 50 mM Tris (pH 7.5), 1 mM EDTA, 150 mM NaCl, 1% Nonidet P-40, 1 mM DTT, 1 mM sodium orthovanadate, and 4 µg/mL of the protease inhibitors aprotinin, leupeptin, and pepstatin.

"Heavy" lysates were flowed over a phosphoTyr peptide library affinity matrix and "light" lysates were flowed over a corresponding unphosphorylated peptide library affinity matrix. Bound proteins were eluted with 250 µl of 20 mM sodium phenylphosphate (pH 7.8). The entire screening protocol was conducted at 4° C. Eluates from the pTyr and Tyr columns were combined, the volume was condensed using a speed vacuum, and the entire SILAC sample was run on one lane of a SDS-PAGE gel.

The SDS-PAGE lane containing the SILAC-labeled proteins was cut into ten pieces and each gel piece was digested with trypsin at pH 8.3 at 37° C. overnight. The peptide mixtures were then extracted from the gel pieces with 40% acetonitrile/2% formic acid and separately injected onto a reverse-phase self-packed C$_{18}$ 75 µM id×10 cm length microcapillary column (New Objective Inc., Woburn, Mass.). Liquid chromatography tandem spectrometry (LC-MS/MS) was performed using a QSTAR Pulsar I quadrupole-TOF (qTOF) mass spectrometer (Applied Biosystems/MDS Sciex, Framingham, Mass.) operated in positive ion data-dependent mode with one MS survey scan followed by three MS/MS scans using a two-minute exclusion window. The nanoflow LC was operated at a flow rate of 275 nL/min using a gradient of 5% B to 38% B over 60 minutes followed by a wash at 95% B and 1% B column for re-equilibration. The buffers consisted of 0.1% acetic acid/0.9% acetonitrile/99% water (A buffer) and 0.1% acetic acid/0.9% water/99% acetonitrile (B buffer).

Proteins were identified and SILAC ratios were determined using the Paragon algorithm in ProteinPilot software, commercially available from Applied Biosystems (Framingham, Mass.). The raw .wiff files were searched for both protein identification from the MS/MS scans and quantitative heavy: light ratios from the MS scan against the reversed SwissProt protein database (Geneva, Switzerland) with a 95% confidence interval. The false positive rate was determined to be less than 3%. The SILAC ratios for each protein identified were plotted by protein number versus the average heavy: light ratio for each peptide of those proteins visible by silver stain that selectively bound to the phosphoTyr peptide library matrix also identified known phosphoTyr binding proteins as well as pyruvate kinase (FIG. 1c). Silver stained SDS-PAGE gel pieces were excised and digested, and peptides extracted as described above. The peptide mixtures were then analyzed by positive ion data dependent microcapillary LCMS/MS using a LTQ 2D linear ion trap mass spectrometer (Thermo Fisher Scientific, San Jose, Calif.). One MS scan was followed by eight MS/MS scans. The LC conditions were the same as the SILAC experiment above except the gradient was shortened to 30 minutes. Proteins were identified by searching the reversed NCBI non-redundant protein database using the Sequest algorithm in Proteomics Browser Software (Thermo Fisher Scientific, San Jose, Calif.). The results were filtered using Xcorr cut-offs of 2.0 for 1+ ions, 2.0 for 2+ ions, and 2.75 for 3+ ions, as well as Sf scores of 0.4 for all charge states. At least two peptides per protein were necessary for identification. The false positive rate was determined to be less than 2%.

To confirm the preferential binding of pyruvate kinase to the phosphoTyr peptide affinity matrix, eluates from the phosphoTyr and Tyr peptide library columns were analyzed by Western blot using a pyruvate kinase antibody (FIG. 1d). Western blot analysis was carried out according to standard protocols. The following antibodies were used: flag (Sigma), pyruvate kinase (Abcam), GAPDH (Abcam), pan-p85 (Upstate). p85, the 5H2 domain-containing regulatory subunit of P13K, was used as a positive control, and GAPDH was used as a negative control. As shown in FIG. 1d, immunoblotting for both p85 and pyruvate kinase shows selective binding to the phosphoTyr peptide library matrix.

Example 2

Phosphopeptide Binding is Specific to the M2 Isoform of Pyruvate Kinase

Four pyruvate kinase isoforms exist in mammals: L (liver), R (red blood cell), M1 (adult), and M2 (embryonic/tumor)

(Jurica et al., *Structure* 6: 195-210, 1998). The M1, M2, and L isoforms were transiently expressed as flag-tagged proteins in 293 cells, and lysates were flowed over the phosphoTyr and Tyr peptide affinity columns to assess binding. Eluates from the columns were analyzed by Western blot using a flag antibody, as described above (FIG. 2a). The M2 isoform is the only pyruvate kinase isoform that binds phosphoTyr peptides. PKM1 and PKM2 are identical proteins with the exception of a 56 amino acid stretch encoded by the alternatively-spliced region. Previous studies have shown that this stretch of amino acids comprises the only structural difference between the M1 and M2 isoforms and forms an allosteric pocket unique to PKM2 that allows for binding of its activator, FBP (Dombrauckas et al., *Biochemistry* 44: 9417-29, 2005).

To determine if the FBP binding pocket on PKM2 coordinates phosphoTyr peptide binding, it was assessed whether FBP could compete for binding of PKM2 to a phosphoTyr peptide library column. Recombinant protein was synthesized by cloning human PKM2 into a pET28a vector (Novagen) at NdeI and BamHI sites and PKM2 was expressed as a N-terminal $His_6$ tag fusion protein. The protein was expressed and purified with a standard protocol. Briefly, pET28a-PKM2 was transformed into BL2 I (DE3)pLysS cells and grown to an $OD_{600}$ of 0.8 and induced with 0.5 mM IPTG for seven hours at room temperature. Cells were lysed using lysozyme in lysis buffer (50 mM Tris, pH 8.0, 10 mM $MgCl_2$, 200 mM NaCl, 100 mM KCl, 20% glycerol, 10 mM imidazole, 1 mM PMSF). The cell lysate was cleared by centrifugation. PKM2 was purified by batch binding to Ni—NTA resin (Qiagen). The resin was then washed with lysis buffer containing 30 mM imidazole for 200 column volumes, and $His_6$-tag-PKM2 was eluted with 250 mM imidazole. The protein was dialyzed overnight at 4° C. to remove the imidazole.

Figure 2:
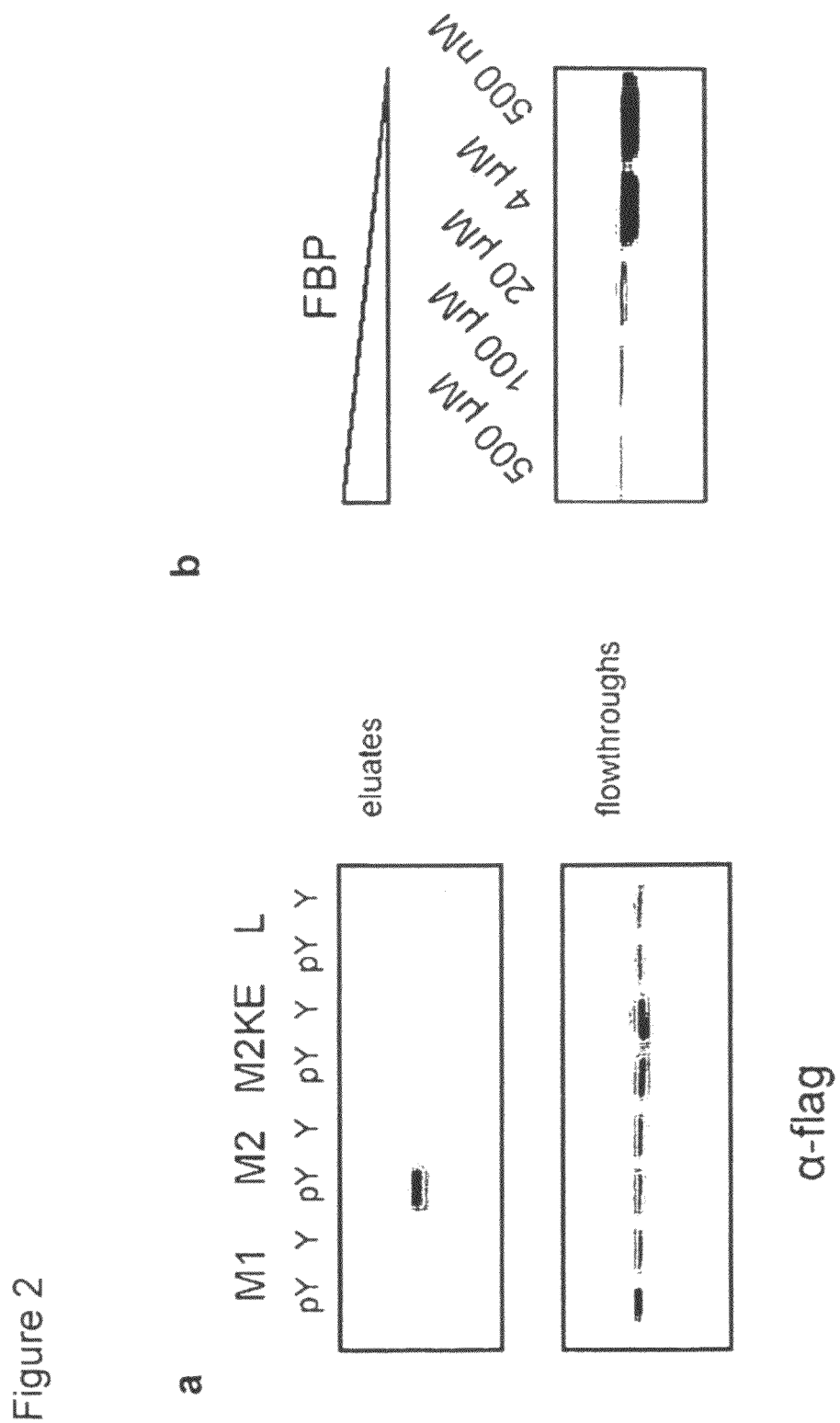
FIG. 2 shows that phosphopeptide binding is specific to the M2 isoform of pyruvate kinase and involves Lys433 near the FBP binding pocket.
Figure 3:
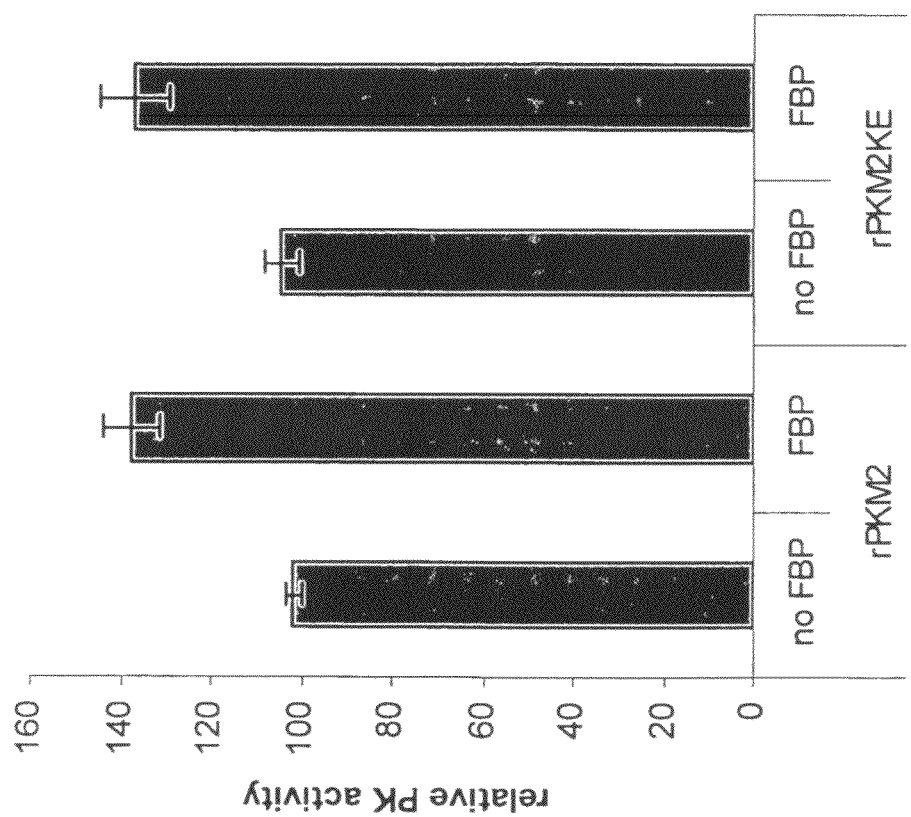
FIG. 3 shows that FBP activated the KE point mutant of PKM2 to a similar extent as the wild-type protein. The activities of recombinant PKM2 and PKM2 KE were assessed in the presence and absence of saturating amounts of FBP (100 μM). Bars denote standard deviation (n=3).

Recombinant PKM2 was incubated with increasing amounts of FBP and then flowed over the phosphoTyr peptide affinity matrix. 20 μM FBP was able to compete for binding of recombinant PKM2 to phosphoTyr peptides (FIG. 2b). To further examine how this region of PKM2 interacts with phosphoTyr, point mutants of various residues in and around the FBP binding pocket of PKM2 were constructed. While mutation of residues within the FBP binding pocket of PKM2 did not affect phosphoTyr peptide binding (data not shown), mutation of lysine 433 (K433), which lies at the lip of the pocket, to glutamate abolished phosphoTyr peptide binding (FIG. 2a). The K433E (KE) point mutant of PKM2 that lacks phosphoTyr peptide binding ability is activated by FBP to a similar degree as the wild-type protein (FIG. 3). These data suggest that phosphoTyr peptides are binding to PKM2 near the FBP binding pocket of the enzyme and that K433 is important for this interaction.

Figure 4:
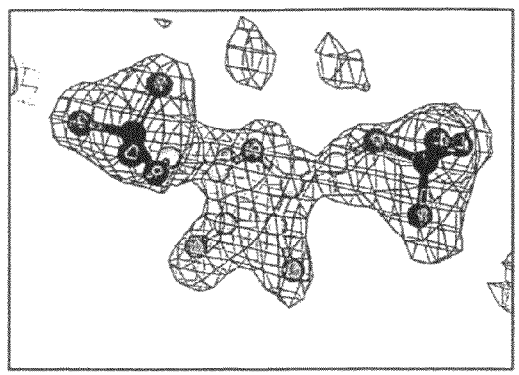
FIG. 4 shows that the phosphotyrosine peptide catalyzes the release of FBP from PKM2.
Figure 4:
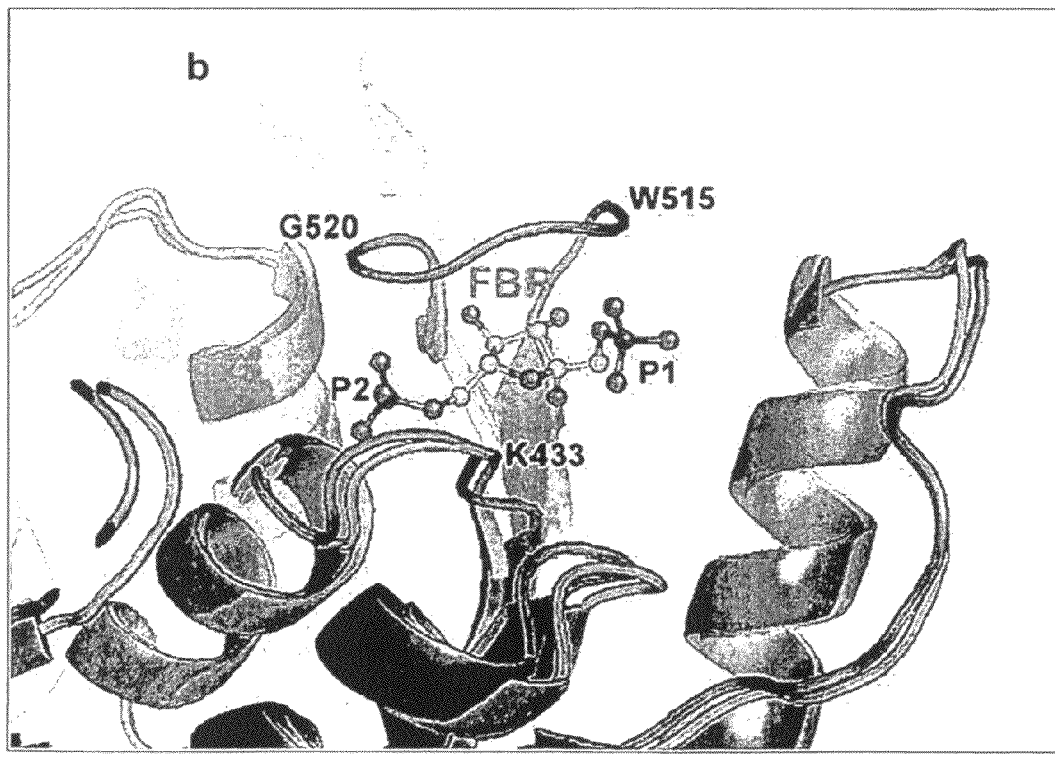
Figure 4:
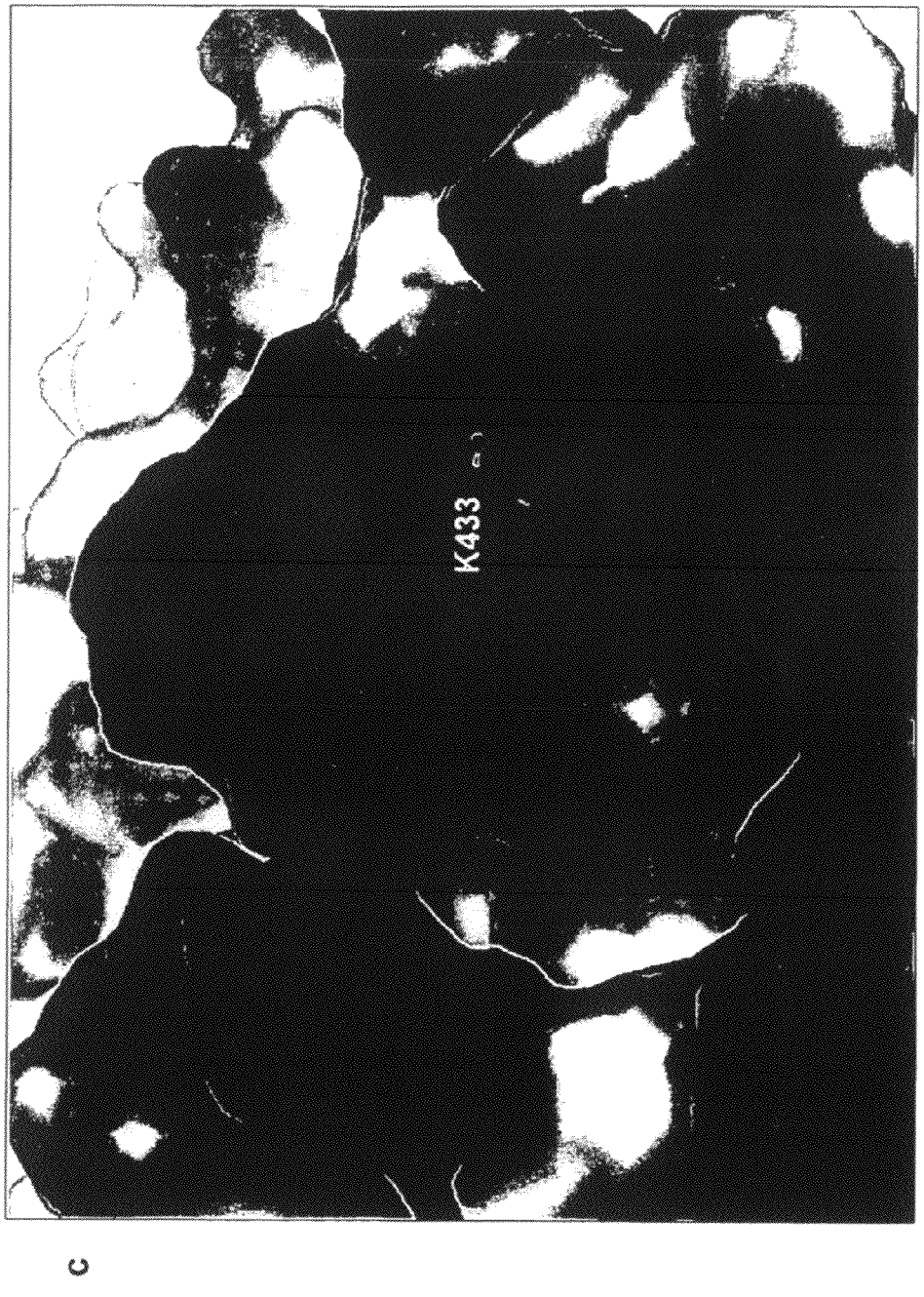

To examine the allosteric FBP binding pocket of PKM2 more closely, x-ray crystallography was used to resolve the structures of both the apo-form (2.5 Å) as well as the FBP bound-form (2 Å) of PKM2. Both forms crystallized as tetramers in the asymmetric unit under physiological pH, with $Mg^{2+}$ and oxalate in the active sites. In the apo crystal, the residues around the FBP binding pocket were not well ordered. In particular, loop W515-G520 had no visible electron density. In comparison, FBP was found in all four allosteric sites in the complex crystal (FIG. 4a), and its presence stabilized many side chains including the W515-G520 loop, K433, and W482 (FIG. 4b). In the FBP-bound form of PKM2, the W515-G520 loop and other side chains were closed down on the FBP molecule, and only the P1 phosphate group of FBP was solvent accessible (FIG. 4c). The fact that ~50% of PKM2 still retained FBP after affinity purification, dialysis, and size-exclusion column chromatography suggests that the release of FBP from the protein is very slow.

Published $K_a$ values for FBP binding to PKM2 are in the micromolar range (Yamada and Noguchi, *Biochem. J.* 337: 1-11, 1999). However, FBP concentrations following protein purification would be orders of magnitude lower than this value. Attempts to measure the dissociation constant based on Michaelis-Menten kinetics have suggested that FBP binding to PKM2 is non-linear. To test the hypothesis suggested by the above structural studies that FBP tightly binds to PKM2, freshly generated recombinant PKM1 or PKM2 protein was diluted to a concentration of 1 μM in 50 mM Tris (pH 7.5), 100 mM KCl, 5 mM $MgCl_2$, and 5% glycerol. $^{14}$C-FBP (MP Biomedicals) was used at 25× when added to PKM1, PKM2, or the diffusion control, corresponding to a final concentration of ~10 μM $^{14}$C-FBP. The PKM1, PKM2, and no-protein control were incubated with $^{14}$C-FBP for 30 minutes at room temperature and then identified per protein. Proteins with SILAC ratios greater than 3:1 were considered significant pTyr binding proteins.

As shown in FIG. 1b, the majority of the proteins identified had peptides that yielded ~1:1 SILAC heavy to light ratios, thus indicating equal binding to the phosphoTyr and Tyr peptide matrices. As a validation of the approach, several proteins that contain well-characterized phosphoTyr binding domains were identified as showing >3:1 SILAC ratios, consistent with preferential binding to the phosphoTyr peptide library affinity matrix. Despite the absence of a known phosphoTyr binding domain, pyruvate kinase exhibited a ≥15:1 SILAC heavy:light ratio, identifying it as a novel phosphoTyr binding candidate.

As validation of the phosphoTyr binding property of pyruvate kinase, lysates from HeLa cells were passed over the phosphoTyr and Tyr peptide library affinity matrices and eluates were analyzed by SDS-PAGE. LC-MS/MS analysis dialyzed against >2 L of buffer using 10,000 MWCO dialysis cassettes (Pierce) for at least 7 hours. After dialysis, samples were recovered and the amount of $^{14}$C-FBP retained in each dialysis cassette was determined by scintillation counting.

The PKM 1 sample had the same amount of $^{14}$C counts as the no-protein control sample. In contrast, the PKM2 sample exhibited 52±5% more counts than both the PKM1 sample and the no-protein control. Upon further analysis, it was estimated that $^{14}$C FBP is retained at roughly half a mole per mole on the PKM2 protein. Since 50% of the recombinant protein already had bacterial FBP bound, these results are consistent with the retained $^{14}$C-FBP being tightly bound to the protein.

Example 3

Phosphotyrosine Peptide Catalyzes the Release of FBP from PKM2

To examine the effect of phosphoTyr peptide binding on FBP-bound PKM2, a peptide-binding motif for PKM2 was obtained using traditional peptide library screening. Both the phosphorylated (P-M2tide) and unphosphorylated (NP-M2tide) versions of the optimal peptide were synthesized: P-M2tide (GGAVDDDpYAQFANGG SEQ ID NO:1) and NP-M2tide (GGAVDDDYAQFANGG SEQ ID NO:2) (FIG. 5). The FBP-loaded recombinant PKM2 was incubated with P-M2tide or NP-M2tide, the unbound FBP and peptide were dialyzed away, and the counts retained on the PKM2 were measured. Exposure of PKM2 to the control NP-M2tide resulted in a significant amount of FBP remaining bound to PKM2. In contrast, exposure of PKM2 to the P-M2tide resulted in release of the majority of the FBP (FIG. 4e). These results indicate that phosphoTyr peptide binding catalyzes the release of FBP from PKM2.

Next, the ability of phosphoTyr protein binding to catalyze the release of FBP from PKM2 in vivo was tested. To address this, cells were cultured overnight with $^3$H-glucose that can be metabolized to $^3$H-FBP. Flag-tagged PKM2 was immunoprecipitated and the amount of $^3$H bound to PKM2 with and without pervanadate-treatment was determined by scintillation counting. Increasing the levels of phosphoTyr proteins by a 15-minute treatment with pervanadate resulted in a 30±13% reduction in $^3$H that immunoprecipitated with PKM2. These results support the hypothesis that phosphoTyr protein binding can catalyze the release of FBP from PKM2 in vivo.

Example 4

Phosphopeptide Binding Results in Inhibition of PKM2 Activity

To examine the effect phosphoTyr peptide binding has on PKM2 activity, increasing amounts of P-M2tide and NP-M2tide were incubated with recombinant PKM2 and the enzyme activity of PKM2 was measured. Pyruvate kinase activity was measured according to published methods by a continuous assay coupled to lactate dehydrogenase (LDH). The change in absorbance at 340 nm due to oxidation of NADH was measured using a Victor$^3$ 1420 Multilabel Counter spectrophotometer (PerkinElmer, Inc.). Kinetic assays for activity determinations contained recombinant PK (20-100 ng) or cell lysate (1-2 μg), Tris (pH 7.5) (50 mM), KCl (100 mM), MgCl$_2$ (5 mM), ADP (0.6 mM), PEP (0.5 mM), NADH (180 pM), FBP (10 pM), and LDH (8 units).

Figure 6:
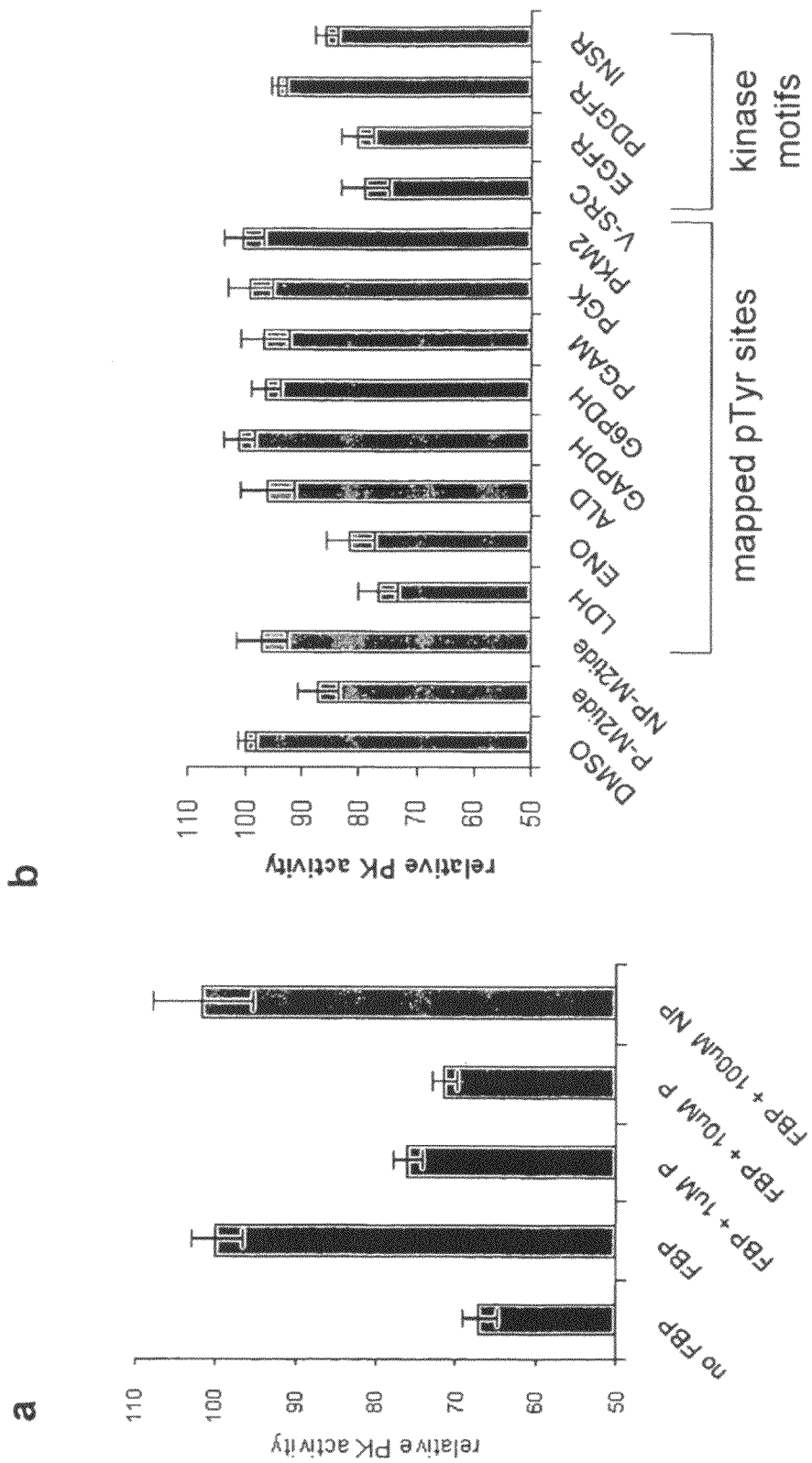
FIG. 6 shows that phosphopeptide binding results in inhibition of PKM2 activity.
Figure 6:
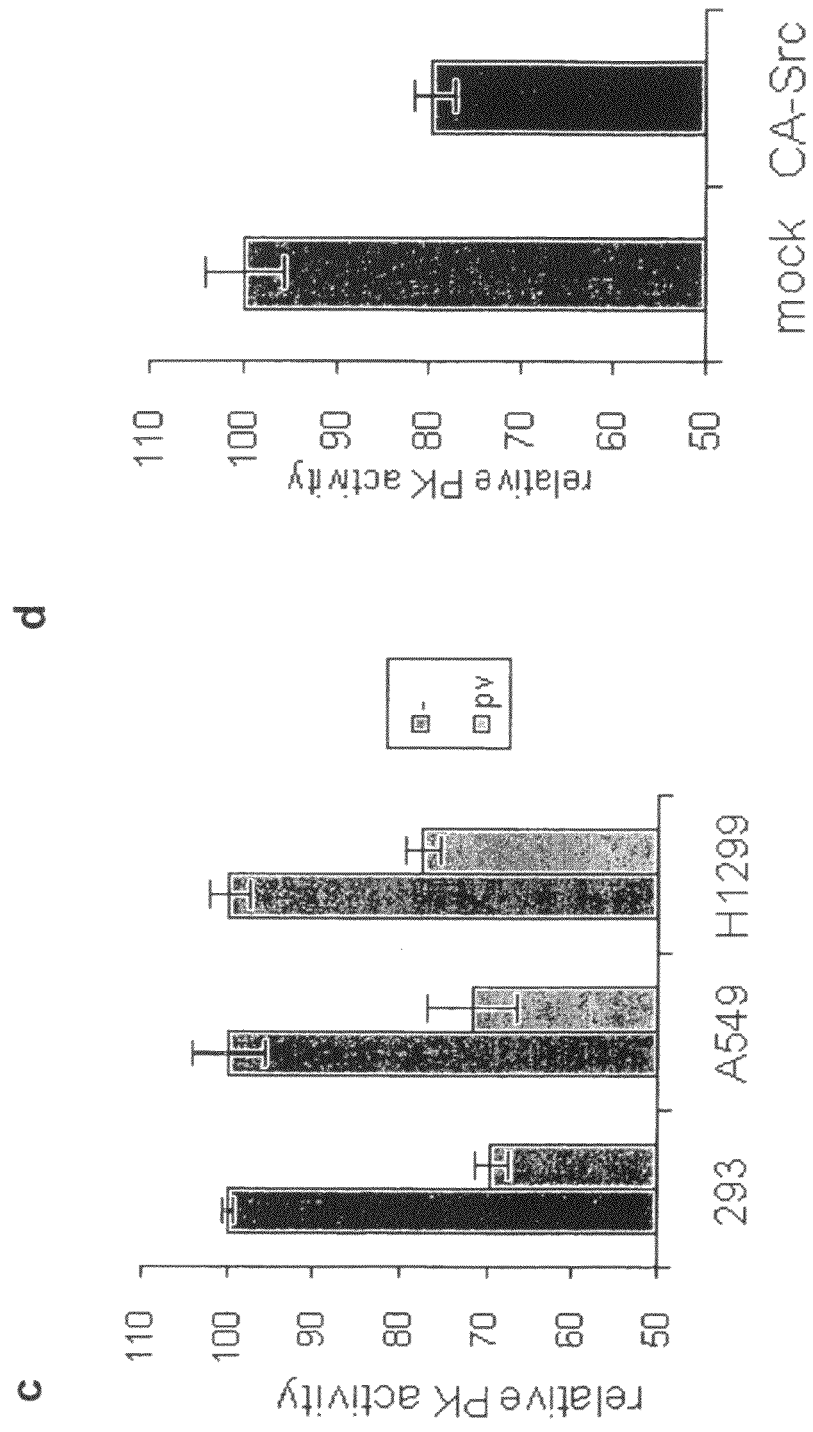
Figure 6:
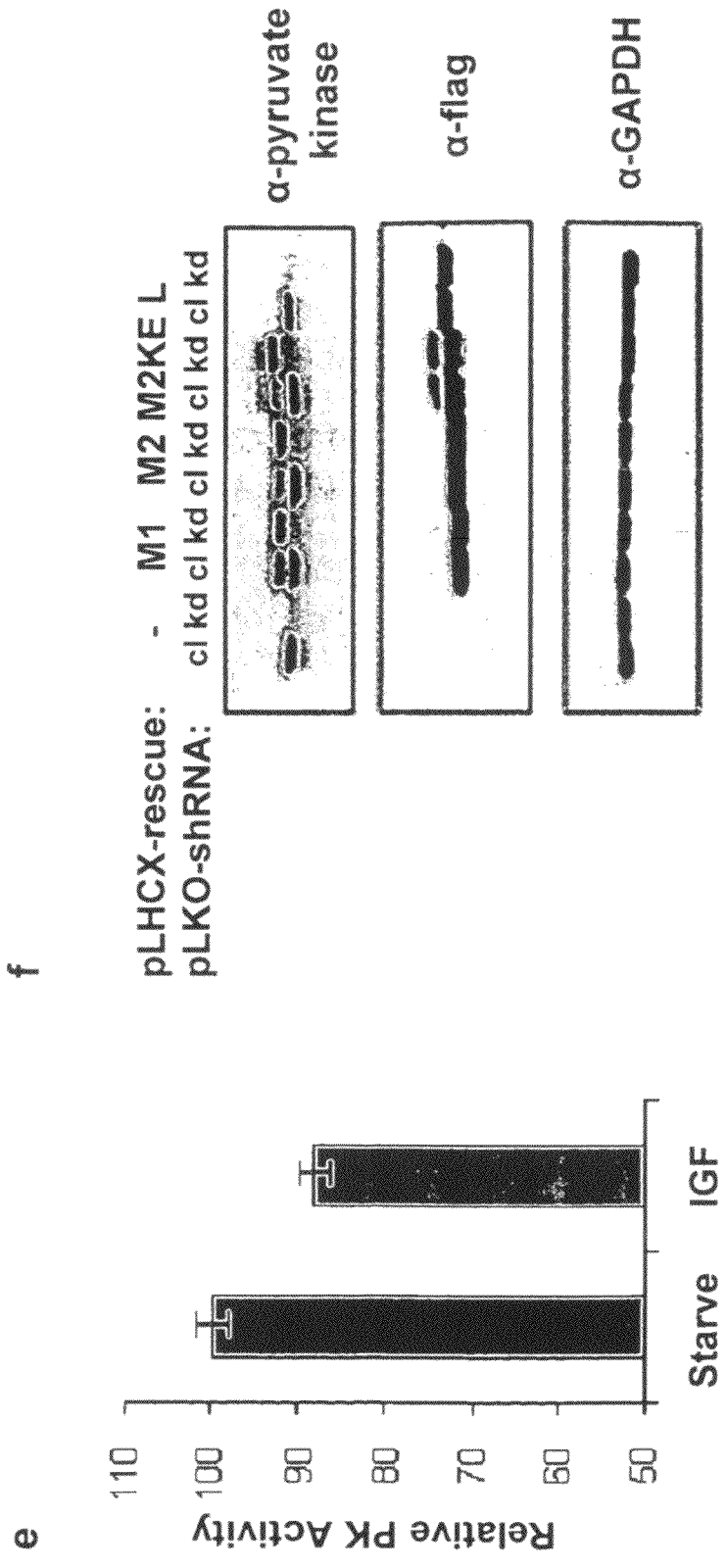
Figure 6:
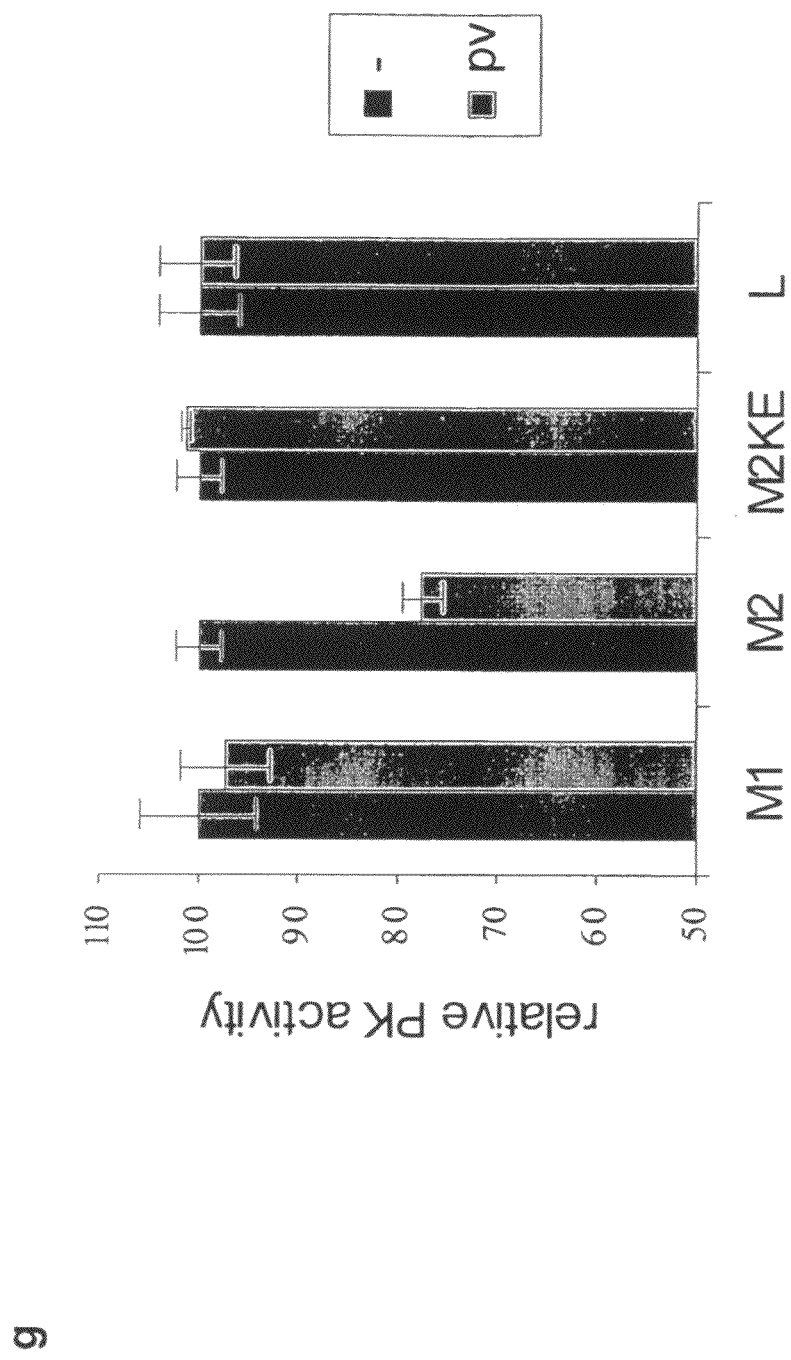

As shown in FIG. 6a, P-M2tide exposure caused a 20-30% inhibition of PKM2 activity in a dose-dependent manner. Multiple phosphoTyr peptides comprising in vivo phosphorylation sites previously identified on metabolic proteins (Villen et al., *Proc. Natl. Acad. Sci. USA* 104: 1488-93, 2007) were synthesized. Several of these phosphoTyr peptides, as well as multiple phosphoTyr peptides designed after known tyrosine kinase motifs, were also shown to inhibit PKM2 activity (FIG. 6b). Notably, the Src kinase motif, along with the in vivo Src kinase sites on enolase and lactate dehydrogenase, were able to inhibit PKM2 activity in vitro.

To address whether PKM2 activity is regulated by tyrosine phosphorylation levels in vivo, phosphoTyr levels were elevated in various cell lines by pervanadate stimulation and pyruvate kinase activity was measured. As shown in FIG. 6c, pervanadate stimulation in three different cancer cell lines resulted in a 20-30% decrease in total pyruvate kinase activity. To assess whether tyrosine kinase intracellular signaling could regulate PKM2 activity in vivo, we tested the effects of overexpressing a tyrosine kinase and stimulating a RTK signaling pathway. Transient overexpression of constitutively active Src kinase in 293 cells resulted in inhibition of PKM2 activity (FIG. 6d). Additionally, acute stimulation of tyrosine kinase signaling by IGF-stimulation in A549 cells resulted in inhibition of PKM2 activity (FIG. 6e). Consistent with earlier studies, this data show that conditions that activate protein-Tyr kinases in cells in culture results in an acute ~15 to 30% reduction in the activity of pyruvate kinase.

Cancer cell lines exclusively express the M2 isoform of pyruvate kinase (Eigenbrodt et al., *Crit Rev Oncol.* 3: 91-115, 1992). However, to confirm that the decrease in pyruvate kinase activity upon increasing phosphoTyr levels was specific to the M2 isoform of pyruvate kinase and that it depended on the ability of PKM2 to bind to phosphoTyr peptides, cell lines that express the M1, M2, L, or M2KE (pTyr binding mutant) forms of pyruvate kinase were constructed (FIG. 6f).

Stable H1299 cells were made that express flag-tagged mouse M1, M2, M2KE, or L. Flag-tagged mouse PKM1, PKM2, PKM2KE, and human PKL were cloned into the retroviral vector pLHCX (Clontech) and were contransfected into 293T cells along with an expression vector with an Ampho cassette. Retrovirus was harvested 36 hours post transfection, and 5 μg/ml polybrene was added. Subconfluent H1299 and A549 cells were infected with harvested retrovirus and were selected in 350 μg/ml hygromycin for two weeks.

The endogenous PKM2 was stably knocked down using shRNA expression. shRNA constructs were provided by Dr. William Hahn (RNAi consortium, Boston, Mass.) in lentiviral cassettes. An shRNA with high PK knockdown efficiency was used (kd) and a control shRNA with no effect on PK levels was also used (ci). Lentivirus was made using a three plasmid packaging system as described previously (Root et al., *Nat. Methods* 3: 715-9, 2006). As shown in FIG. 6f, we obtained efficient knockdown of the endogenous PKM2, and the flag-tagged rescue proteins were expressed to similar, near endogenous levels. Pervanadate-stimulation of the M1-, M2-, M2KE-, and L-expressing knockdown cells resulted in specific inhibition of pyruvate kinase activity only in the wild-type M2-expressing cells. Together, these data suggest that the regulation of pyruvate kinase activity by phosphoTyr levels in vivo is specific to the M2 isoform and requires the phosphoTyr peptide binding capability (FIG. 6g). Similar results were also obtained in A549 cells (data not shown).

Example 5

Figure 7A:
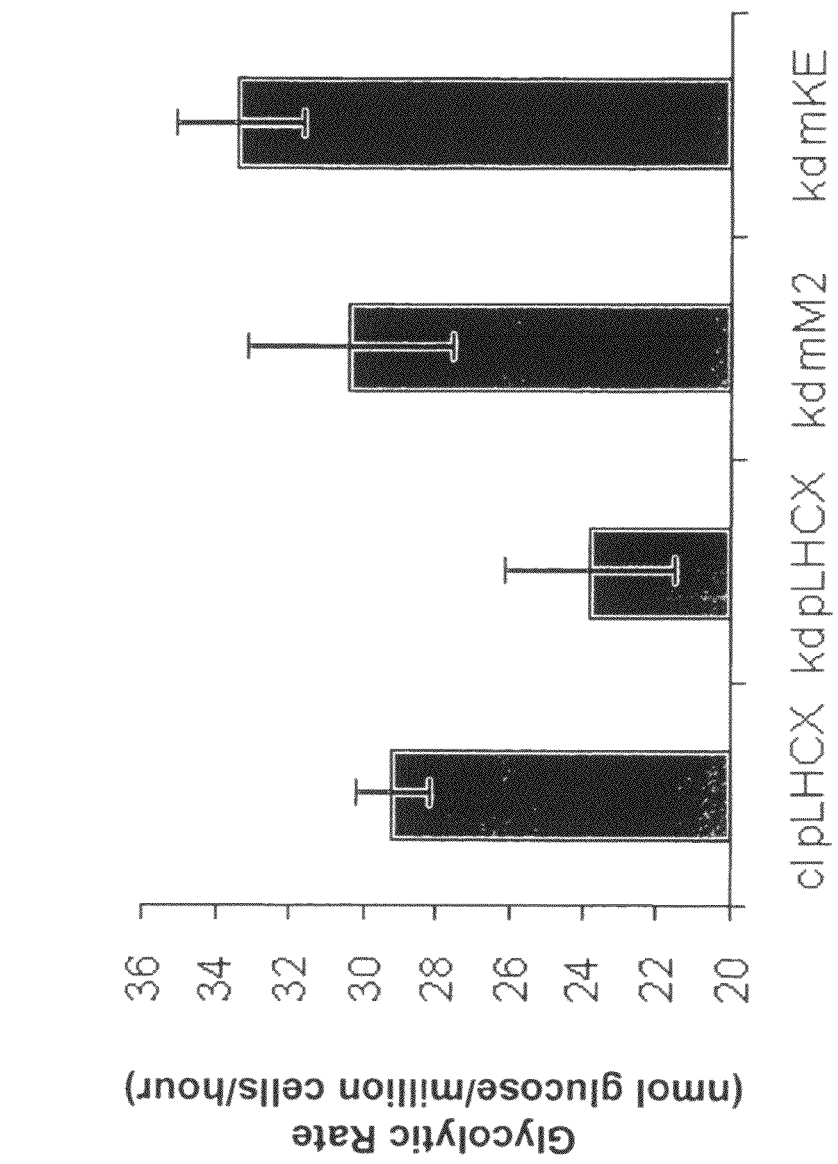
Figure 7:
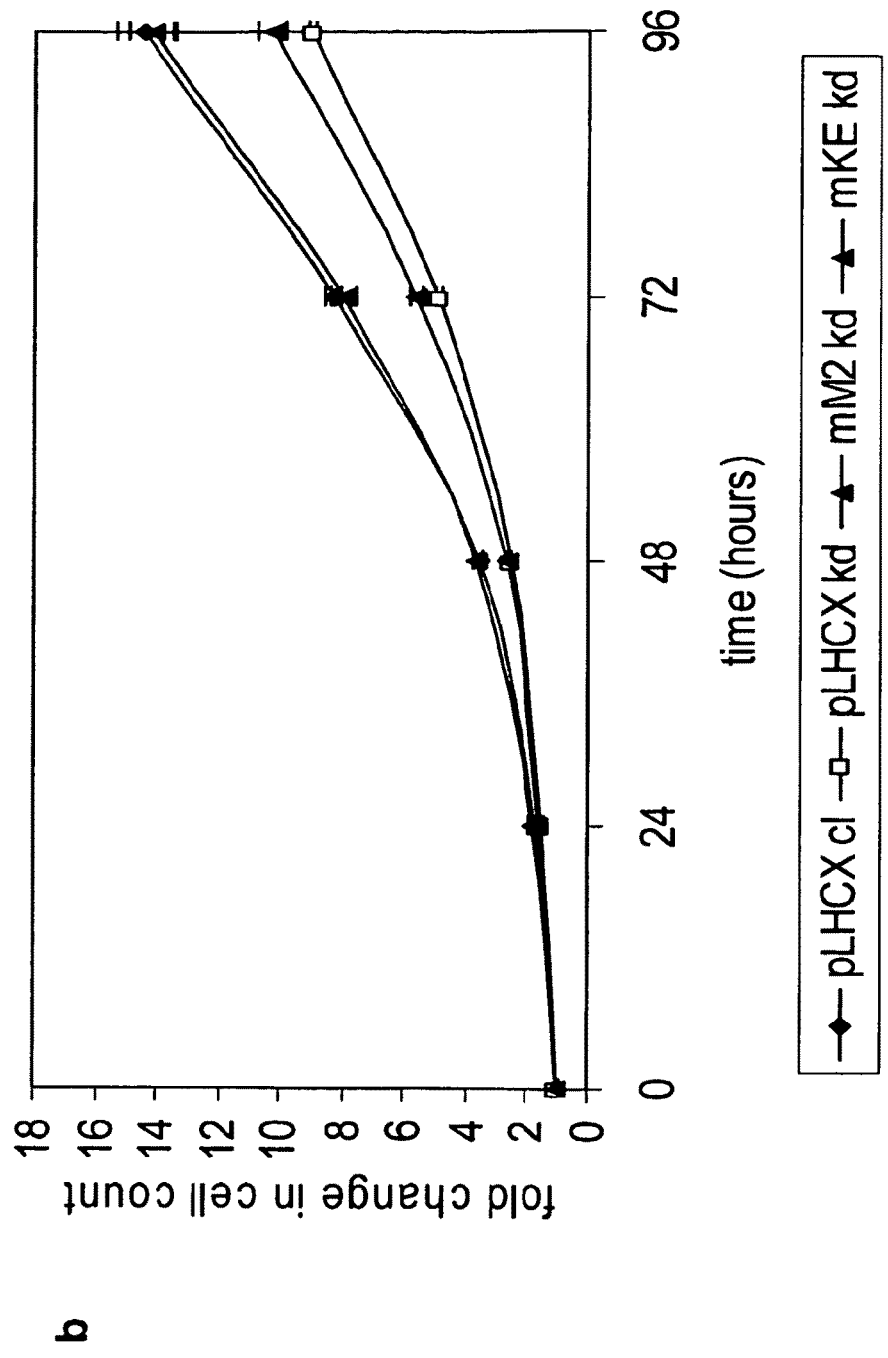
FIG. 7 shows that the phosphopeptide binding ability of PKM2 is critical for cell proliferation, but not for glycolysis. It also shows that activating PKM2 may be an effective way to inhibit cell growth.

The Phosphopeptide-Binding Ability of PKM2 is Essential for Cancer Cell Proliferation To determine whether the regulation of PKM2 activity by phosphoTyr peptide binding has a biological role in the cell, the ability of the phosphoTyr binding mutant, M2KE, to rescue M2 knockdown in cancer cell lines was assessed. Knockdown of PKM2 expression in H1299 lung cancer cells results in reduced glycolysis and decreased cell proliferation (FIGS. 7a and 7b). Both the wild-type mouse M2 and mouse M2KE rescue PK activity (data not shown) and glycolysis in PKM2 knockdown cells (FIG. 7a). Cellular glycolysis rates were measured by following the conversion of 5-$^3$H-glucose to $^3$H$_2$O as described previously (Vander Heiden et al., *Mol Cell Biol.* 21: 5899-912, 2001). The assay was performed with cells attached to tissue culture plates. Briefly, the cells were washed once in PBS, prior to incubation in Krebs buffer without glucose for 30 minutes at 37° C. The Krebs buffer was then replaced with Krebs buffer containing 10 mM glucose spiked with 10 μCi of 5-$^3$H-glucose. After one hour, triplicate samples of media were transferred to PCR tubes containing 0.2 N HCl and the amount of $^3$H$_2$O generated was determined by diffusion as described previously.

However, unlike the wild-type mouse M2, the mouse M2KE mutant is unable to rescue the decreased cell proliferation observed in the knockdown cells (FIG. 7b). 5×10$^4$ cells were seeded in triplicate in 6-well plates and accurate cell counts were obtained every 24 hours using a Coulter particle analyzer for a 3-5 day period. Time zero was taken 16 hours post seeding. These data suggest that the phosphoTyr binding ability of PKM2, while dispensable for the role of PKM2 in glycolysis under cell culture conditions, is essential for its role in cell proliferation. Similar results were also obtained in A549 cells (data not shown).

Example 6

Inhibition of PKM2 by PhosphoTyr Impacts Cellular Metabolism

PKM2 is necessary for aerobic glycolysis in tumor cells. Replacement of PKM2 with its more active splice variant, PKM1, was shown to result in reversal of the Warburg effect as judged by reduced lactate production and increased oxygen consumption. Because disruption of phosphoTyr binding observed in the M2KE mutant is predicted to result in a more active PKM2 enzyme, the importance of the phosphoTyr binding ability of PKM2 was assessed for its role in aerobic glycolysis by measuring lactate production and oxygen consumption in cells expressing the M2KE point mutant. Interestingly, similar to the changes that were observed when PKM2 was replaced by PKM1, a 36±3% reduction in lactate production and 24±4% increase in oxygen consumption in the M2KE-expressing cells when compared with the M2-expressing cells was observed. These results suggest that tyrosine kinase regulation of PKM2 activity is involved in mediating the Warburg effect in tumor cells.

No changes in adenine nucleotide levels or the ATP/ADP ratios were observed in M2-versus M2KE-expressing cells, suggesting that this cannot account for the defect in cell proliferation observed in the M2KE-expressing cells. However, acute inhibition of PKM2 activity in proliferating cells by tyrosine kinase signaling may result in a temporary build-up of upstream glycolytic intermediates which can be used by the cell as precursors for fatty acid and nucleic acid synthesis, which could provide an advantage to PKM2-expressing cells for proliferation. Consistent with this model, a 25% increase in the incorporation of metabolites from $^{14}$C-glucose into lipids upon pervanadate-treatment of PKM2-expressing cells was observed. Importantly, no significant increase in $^{14}$C incorporation into lipids is seen in pervanadate-treated cells expressing the KE point mutant of PKM2 deficient in phosphoTyr binding. A similar increase in the incorporation of $^{14}$C-glucose metabolites into lipids was observed upon pervanadate stimulation of 293 cells. In addition, acute pervanadate stimulation resulted in a 36±1% decrease in oxygen consumption in PKM2-expressing cells with only a 15±4% decrease in oxygen consumption in M2KE-expressing cells. These results demonstrate that phosphoTyr-based regulation of PKM2 activity has consequences for metabolism in tumor cells and support the idea that regulation of PKM2 activity by Tyr kinase signaling may enable glucose metabolites to be utilized for anabolic processes.

It is shown herein that the activity of the glycolytic protein, PKM2, can be regulated by Tyr kinase signaling pathways via a novel phosphoTyr binding ability. Binding of phosphoTyr peptides to PKM2 catalyzes the release of FBP and subsequent inhibition of enzymatic activity. It is hypothesized that phosphoTyr protein binding is a transient event that results in a conformational change in PKM2 structure which releases an otherwise tightly bound FBP molecule. Once released, the ambient concentration of FBP at the time of the collision determines whether PKM2 goes into a low activity state or rebinds FBP and is reactivated. In this model, PKM2 only has the ability to undergo dynamic regulation by FBP (as occurs with bacterial, yeast, and liver forms of pyruvate kinase) if a tyrosine kinase pathway is activated. This mechanism may have evolved to insure that fetal tissues only utilize glucose for growth when they are activated by appropriate growth factor receptor protein-Tyr kinases. Cancer cells, by re-expressing PKM2, acquire the ability to utilize glucose for anabolic processes.

Since proliferating cells require de novo fatty acid synthesis as well as DNA replication, one possible model is that regulation of PKM2 activity allows for a balance between ATP production and fatty acid/nucleic acid production. Alternatively, phosphoTyr based regulation of PKM2 enzymatic activity may provide a direct link between cell growth signals utilizing tyrosine kinases and control of glycolytic metabolism. Regardless, these data demonstrate a novel mechanism for phosphoTyr-based regulation of a metabolic protein that is important for cell proliferation.

Example 7

The M2 Splice Isoform of Pyruvate Kinase is Important for Cancer Metabolism and Tumor Growth To confirm that tumor tissues switch PK expression from an adult isoform to the embryonic M2 isoform, antibodies that distinguish PKM1 from PKM2 were generated. Mammary gland tissues from MMTV-NeuNT mice, a breast cancer tumor model, were analyzed before and after tumor development for PK isoform expression. The primary PK isoform prior to tumor development is PKM1; however, the primary isoform from four independent tumors is PKM2. All cell lines examined, including multiple cancer lines derived from different tissues, also exclusively express the M2 isoform of PK. Immunohistochemistry of human colon cancer using the PKM1 and PKM2 specific antibodies shows selective expression of PKM1 in the stromal cells and PKM2 in the cancer cells.

Given that PKM2 is selectively expressed in proliferating cells, its importance for cell proliferation was assessed via short hairpin RNA knockdown. Stable knockdown of PKM2 in the human lung cancer cell line H1299 results in decreased rates of glucose metabolism and reduced cell proliferation. Glucose metabolism was monitored by following the conversion of 5-[$^3$H]-glucose to [$^3$H]-water, which occurs at the enolase step immediately preceding PK. To address whether it is the M2 isoform that is specifically critical for cell proliferation, stable cell lines expressing flag-tagged mouse PKM1 (mM1) or PKM2 (mM2) were made and then stable knockdown of endogenous PKM2 was induced using shRNA expression. Both mM1 and mM2 were able to rescue the glucose metabolism and proliferation defects of the knockdown cells when grown in the artificially high glucose and oxygen conditions of cell culture. Similar results were obtained using A549 cells, and no changes in cell size were observed in either cell line.

To examine whether PKM2 expression enhances tumor cell growth under lowered oxygen and glucose conditions, proliferation rates of the M1 and M2 rescue cells (M2 knockdown cells expressing mM1 or mM2) were measured in physiologic glucose levels and hypoxic oxygen. Proliferation of neither the M1 nor the M2 cells was affected by growth in normal (5 mM) glucose; however, proliferation of the M1 cells was significantly decreased compared to the M2 cells in 0.5% oxygen. The percent decrease in oxygen consumption following addition of subsaturating amounts of oligomycin, a specific inhibitor of mitochondrial ATP synthase, was the same in both the M1 and M2 cells. However, oligomycin-treatment at the same dose affected the proliferation rate of the M1 cells significantly more than the M2 cells. These data suggest that the M1 cells are more dependent on oxidative phosphorylation for cell proliferation.

Consistent with published findings that PKM1 is a more active enzyme than PKM2, it was found that the M1 rescue cells had 60% higher PK activity than the M2 rescue cells. However, the adenine nucleotide levels in the M1 and M2 cells were comparable in normal culture conditions as well as upon treatment with saturating or subsaturating amounts of oligomycin. These data suggest that changes in ATP levels or mitochondrial coupling do not account for the observed changes in proliferation rates in the M1 and M2 cells.

Given the reduced proliferation of the M1 cells in response to both hypoxic conditions and oligomycin treatment, it was hypothesized that the M1 rescue cells may preferentially metabolize glucose by oxidative phosphorylation rather than rely on aerobic glycolysis. To test this hypothesis, oxygen consumption, lactate production, and metabolite levels in the M1 and M2 rescue H1299 cells were compared. It was found that the M1 cells consume more oxygen and produce less lactate than the M2 cells. These differences in oxygen consumption and lactate production were statistically significant ($p<0.02$). Similar results were observed when endogenous PKM2 was replaced with mouse PKM1 or mouse PKM2 in two other invasive cancer cell lines, A549 and SN12C. However, switching PK isoform expression from M2 to M1 in the non-invasive breast cancer cell line known to have low aerobic glucose consumption rates, MCF7, had no significant affect on lactate production and oxygen consumption.

An increase in lactate levels in the H1299 M2 rescue cells was also found by liquid chromatography-mass spectrometry-based (LC-MS) measurement of metabolites. Additional metabolite levels were also different in the M2 cells as compared with the M1 cells. Pyruvate levels were increased, and fructose-bisphosphate levels were decreased in the M2 cells. Together, these data show that the ratio of lactate production to oxygen consumption is higher in the M2 cells than in the M1 cells and that other glycolytic intermediates are affected by differential expression of these PK isoforms.

To determine whether M2 isoform expression is important for tumor cell growth in vivo, xenograft studies using the M1 and M2 rescue cells were performed. Nude mice were injected with 5 million M1 or M2 rescue H1299 cells, and tumor growth was monitored over a seven-week period. Mice injected with the M1 cells showed a delay in tumor development as compared with those injected with the M2 cells. Fewer tumors developed from the M1 cells, and those that did were smaller in size. As judged by total tumor mass, the M2 cells gave rise to significantly larger tumors than the M1 cells. Western blot analysis of the developed tumors shows the flag-tagged rescue mM1 and mM2 proteins are retained in the tumors, however endogenous expression of PKM2 returned in both cases. No tumors were recovered that solely expressed mM1. To determine whether this was the result of loss of shRNA-mediated knockdown of endogenous PKM2 or whether it represented a selective growth advantage for cells expressing M2, a 50/50 mixture of the M1 and M2 cells were injected into nude mice. Tumors that arose from the mixture of M1 and M2 cells only retained expression of the flag-mM2 rescue protein, demonstrating that the majority of the tumor, if not the entire tumor, was derived from the M2-expressing cells. These data show that PKM2 expression provides a selective growth advantage for tumor cells in vivo.

It was shown that the switch to the M2 isoform of PK in tumor cells is necessary to cause the metabolic phenotype known as the Warburg effect. Given that PKM2 is expressed during embryonic development and in many non-transformed cell lines, M2 expression alone is unlikely a transforming event. Rather, the presence of PKM2 may contribute to a metabolic environment that is amenable to cell proliferation. While not wishing to be bound by theory, an attractive hypothesis is that PKM2, which undergoes complex regulation by both fructose-1,6-bisphosphate and protein-Tyr kinase signaling, provides the flexibility to distribute glucose metabolites into anabolic versus catabolic processes, depending on the demands of rapidly growing cells. It remains unclear, however, why more of the pyruvate made in PKM2-expressing cells is converted to lactate while more of the pyruvate generated in PKM1 cells is metabolized in the mitochondria. One explanation is that M2 expression results in higher expression of lactate dehydrogenase. Alternatively, M2 expression could lead to reduced mitochondrial density and decreased expression of proteins involved in oxidative phosphorylation. To test these hypotheses, we analyzed the expression of the lactate dehydrogenase and $F_1F_0$-ATPase proteins in the M1 and M2 cells. No differences in the protein levels were detected; however, differential activities of lactate dehydrogenase, pyruvate dehydrogenase, and/or pyruvate dehydrogenase kinase, or proteins involved in oxidative phosphorylation in the M1 and M2 cells could account for the observed shift to aerobic glycolysis in the M2-expressing cells.

It is also possible that the M2 isoform of PK has functions independent of its role in glycolysis. GAPDH has been identified to be part of a transcription factor complex, and the M2 isoform of PK may have a role in caspase-independent cell death. In addition, PKM2 has the unique ability among PK isoforms to interact with tyrosine-phosphorylated proteins. It is therefore possible that such an alternative function of PKM2 independent of its enzymatic activity promotes aerobic glycolysis and tumor growth.

Dependence on PKM2-mediated aerobic glycolysis for tumor growth is likely to be variable in cancer cells given the reliance of some tumors on alternative energy sources such as fatty acid oxidation. This idea is supported by the finding that replacement of PKM2 with mouse PKM1 in the MCF7 cancer cell line had no effect on glucose metabolism as measured by lactate production and oxygen consumption. Glutamine metabolism has also recently been identified as an important source of mitochondrial fuel in cancer cells. It is possible that differences in glutamine metabolism may contribute to the metabolic phenotypes of PKM1 and PKM2 cells.

A difference between the M1 and M2 isoforms of PK is that M2 is a low activity enzyme that relies on allosteric activation by the upstream metabolite, fructose-1,6-bisphosphate, whereas M1 is a constitutively active enzyme. Additionally, the activity of the M2 isoform (but not the M1 isoform) can be inhibited by tyrosine kinase signaling in tumor cells. Decreased M2 activity as a result of growth factor stimulated-kinase signaling pathways would be predicted to build up phosphoenolpyruvate levels, which would result in inhibition of the isoform of phosphofructokinase-2 expressed in tumor cells, PFKFB3. This would result in reduced fructose-2,6-bisphosphate levels which would in turn reduce fructose-1,6-bisphosphate levels. This type of regulation is consistent with the results showing a significant reduction in fructose-bisphosphate levels in the M2 cells as compared with the M1 cells. It is therefore possible that differential levels of fructose-bisphosphate or other upstream metabolites in the glycolytic pathway mediate the switch to aerobic glycolysis from oxidative phosphorylation in M2-expressing cells by an as yet unexplained mechanism. An alternative explanation is that M1 preferentially shuttles pyruvate to the mitochondria or M2 preferentially shuttles pyruvate to lactate dehydrogenase. For example, tyrosine phosphorylation of lactate dehydrogenase could facilitate its binding to PKM2, thereby channeling the product of PK to lactate. Regardless of the mechanism by which PKM2 promotes the Warburg effect, the finding that M2 expression is advantageous for tumor cell growth in vivo demonstrates that the unique metabolism of tumor cells is critical for tumorigenesis.

Methods Summary

Cells were lysed in Nonidet P-40 lysis buffer, and Western blot analysis was carried out according to standard protocols. Paraffin embedded colon cancer and control tissues were stained with polyclonal PKM1 and PKM2 antibodies using an automated immunostainer and analyzed using IHC kits and EDTA-based antigen retrieval (Ventana Medical Systems). For cell line construction, flag-mouse PK isoforms were cloned into pLHCX and used to make retrovirus to infect H1299, A549, SN12C, and MCF7 cells. After two weeks of selection in 350 µg/ml hygromycin (150 µg/ml hygromycin for MCF7), the stable cells expressing flag-mouse PK were infected with lentivirus containing knockdown or control shRNA towards human PKM2. These cells were selected for one week in 2 µg/ml puromycin prior to experimentation. Cellular glucose metabolism rates were measured by following the conversion of $5-^3H$-glucose to $^3H_2O$ as described previously (Vander Heiden et al., *Mol Cell Biol* 21: 5899-912, 2001). Cellular proliferation rates were determined by seeding $5 \times 10^4$ cells in triplicate in 6-well plates and taking cell counts every 24 hours using a Coulter particle analyzer for a 3-5 day period. PK activity was assessed using a continuous assay coupled to lactate dehydrogenase. Adenine nucleotide levels were measured using an ATP bioluminescence assay kit (Roche) as well as by HPLC as described previously (Budinger et al., *Am J Physiol.* 270: L44-53, 1996). Lactate production was measured using a fluorescence-based assay kit (BioVision). Oxygen consumption rates were measured using an anaerobic chamber fitted with a polarographic oxygen electrode as described previously (Vander Heiden et al., *Mol Cell Biol.* 21: 5899-912, 2001). Metabolite extracts were prepared from $2 \times 10^7$ cells using cold 80% ethanol, 0.1% formic acid. After centrifugation, the metabolite extracts were dried under nitrogen, reconstituted in water, and analyzed by LC-MS as described previously (Sabatine et al., *Circulation* 112: 3868-75, 2005). Nude mice were injected subcutaneously with $5 \times 10^6$ H1299 cells as described previously (Engelman et al., *J Clin Invest.* 116: 2695-706, 2006). Tumor formation was assessed every 2-3 days, and the tumors were dissected and weighed at seven weeks post-injection.

All cell lines were purchased from ATCC and cultured according to ATCC protocols. Cells were lysed in buffer containing 50 mM Tris pH 7.5, 1 mM EDTA, 150 mM NaCl, 1% Nonidet P-40, 1 mM DTT, 4 µg/ml aprotinin, 4 µg/ml leupeptin, and 4 µg/ml pepstatin. After homogenization, mouse tissues were lysed in buffer containing 25 mM Tris pH 7.4, 10 mM EDTA, 10 mM EGTA, 100 mM NaF, 50 mM NaPPi, 1% Nonidet P-40, 1 mM DTT, 4 µg/ml aprotinin, 4 µg/ml leupeptin, and 4 µg/ml pepstatin. Western blot analysis was carried out according, to standard methods. The following commercial antibodies were used as probes: pyruvate kinase (Abcam), GAPDH (Abcam), actin (Sigma), and flag (Sigma).

Archived paraffin embedded tissue from a patient previously diagnosed with colon cancer and from a normal control (both from Children's Hospital Boston) were stained with polyclonal antibodies to PKM1 and PKM2 using an automated immunostainer and analyzed using immunohistochemistry kits and EDTA-based antigen retrieval (Ventana Medical Systems, Tucson, Ariz.). Results were photographed using an Olympus BX50 microscope and an Olympus QColor3 camera.

Flag-tagged mouse PKM1 and PKM2 were cloned into the retroviral vector pLHCX (Clontech) and were cotransfected into 293T cells along with an expression vector with an Ampho cassette. Retrovirus was harvested 36 hours post transfection, and 5 µg/ml polybrene was added. Subconfluent H1299, A549, and SN12C cells were infected with harvested retrovirus and were selected in 350 µg/ml hygromycin for 2 weeks. MCF7 cells were infected and selected in 150 µg/ml hygromycin for 2 weeks.

shRNA constructs were provided by Dr. William Hahn (RNAi consortium) in lentiviral cassettes. A shRNA with high PK knockdown efficiency was used (kd) (CCGGGCT-GTGGCTCTAGACACTAAAC-TCGAGTTTAGTGTCTA-GAGCCACAGCTTTTTG SEQ ID NO:3), and a shRNA with no effect on PK levels was used as a control (cl) (CCGG-GAGGCTTCTTATAAGTGTTTACTCG-AGTAAACACT-TATAAGAAGCCTCTTTTTG SEQ ID NO:4). As described previously (Root et al., *Nat Methods* 3: 715-9, 2006), lentivirus was made using a three plasmid packaging system. Briefly, shRNAs in the pLKO.1-puro vector were cotransfected into 293T cells along with expression vectors containing the gag/pol, rev, and vsvg genes. Lentivirus was harvested 48 hours post transfection, and 5 µg/ml polybrene was added. Subconfluent H1299 and A549 cells were infected with harvested lentivirus, and were selected in 2 µg/ml puromycin for one week.

Cellular glucose metabolism rates were measured by following the conversion of $5-^3H$-glucose to $^3H_2O$ as described previously (Vander Heiden et al., *Mol Cell Biol* 21: 5899-912, 2001). The assay was performed with cells attached to tissue culture plates. Briefly, the cells were washed once in PBS, prior to incubation in Krebs buffer without glucose for 30 minutes at 37° C. The Krebs buffer was then replaced with Krebs buffer containing 10 mM glucose spiked with 10 µCi of $5-^3H$-glucose. After one hour, triplicate samples of media were transferred to PCR tubes containing 0.2 N HCl and the amount of $^3H_2O$ generated was determined by diffusion as described previously (Vander Heiden et al., *Mol Cell Biol* 21: 5899-912, 2001).

$5 \times 10^4$ cells were seeded in triplicate in 6-well plates and accurate cell counts were obtained every 24 hours using a Coulter particle analyzer for a 3-5 day period. Time zero was taken 16 hours post-seeding. Cells grown in low oxygen were incubated in a sealed hypoxia chamber set to 0.5% oxygen. Cells grown in the presence of oligomycin were treated with 125 nM oligomycin at time zero.

Pyruvate kinase activity was measured by a continuous assay coupled to lactate dehydrogenase (LDH). The change in absorbance at 340 nm due to oxidation of NADH was measured using a Victor$^3$ 1420 Multilabel Counter spectrophotometer (PerkinElmer, Inc.). Kinetic assays for activity determinations contained cell lysate (1-2 µg), Tris pH 7.5 (50 mM), KCl (100 mM), MgCl$_2$ (5 mM), ADP (0.6 mM), PEP (0.5 mM), NADH (180 µM), FBP (10 µM), and LDH (8 units).

ATP levels were assessed using an ATP bioluminescence assay kit (Roche). Adenine nucleotides were also measured by HPLC as described previously (Budinger et al., *Am J Physiol.* 270: L44-53, 1996). Briefly, for each sample, 6 million cells were resuspended in 300 µl of media. 20 µl of 1 M HClO$_4$ was added and this solution extracted with 11.75/13.25 (v/v) mixture of tri-noctylamine/fluorotrichloromethane. The aqueous phase was recovered and applied to a Zorbax Rx C8 column and eluted with a linear gradient of 90% buffer A (50 mM KH$_2$PO$_4$, 8 mM tetrabutylammonium hydrogen sulfate (TBAS pH 5.8)/10% buffer B (50 mM KH$_2$PO$_4$, 8 mM TBAS, pH 5.8, 40% acetonitrile) to 55% buffer A/45% buffer B over 15 minutes. Adenine nucleotides were detected spectrophotometrically (254 nm). ATP, ADP, and AMP peaks within each sample were confirmed by coinjection of each nucleotide with each sample. Standard curves were determined for ATP, ADP and AMP to facilitate quantitation the nucleotides in each sample.

Cellular oxygen consumption rates were measured using a water-jacketed (37° C.) anaerobic chamber fitted with a polarographic oxygen electrode as described previously (Vander Heiden et al, *Mol Cell Biol* 21: 5899-912, 2001). The electrode was calibrated with 150 mM NaCl equilibrated to room air at 37° C. (corresponding to 199 nmol O$_2$/ml).

Lactate production was measured using a commercially-available fluorescence-based assay kit (BioVision). Fresh media was added to a 12-well plate of subconfluent cells, and aliquots of media from each well were assessed one hour later for amount of lactate present. Cell number was determined using a Coulter particle analyzer.

Metabolite extracts were prepared from 2×10$^7$ cells using 2 ml ice-cold 80% ethanol containing 0.1% formic acid. Extracts were centrifuged at 10,000 rpm for 20 minutes at 4° C., and the supernatant was dried under a nitrogen flow. The dried extract was reconstituted in 400 µl water, and the insoluble fraction was spun down at 10,000 rpm for 20 minutes at 4° C. 200 µl of the supernatant was loaded into 96 well plates, and the LC-MS analysis of metabolites was performed as described previously (Sabatine et al., *Circulation* 112: 3868-75, 2005).

Nude mice (nu/nu, male 6-8 week old, Charles River Laboratories) were injected subcutaneously with 5×10$^6$ H1299 cells. Tumor formation was assessed every 2-3 days. At seven weeks post-injection, the tumors were dissected and weighed.

Example 8

Inhibitors and Activators of PKM2 Activity

Figure 8:
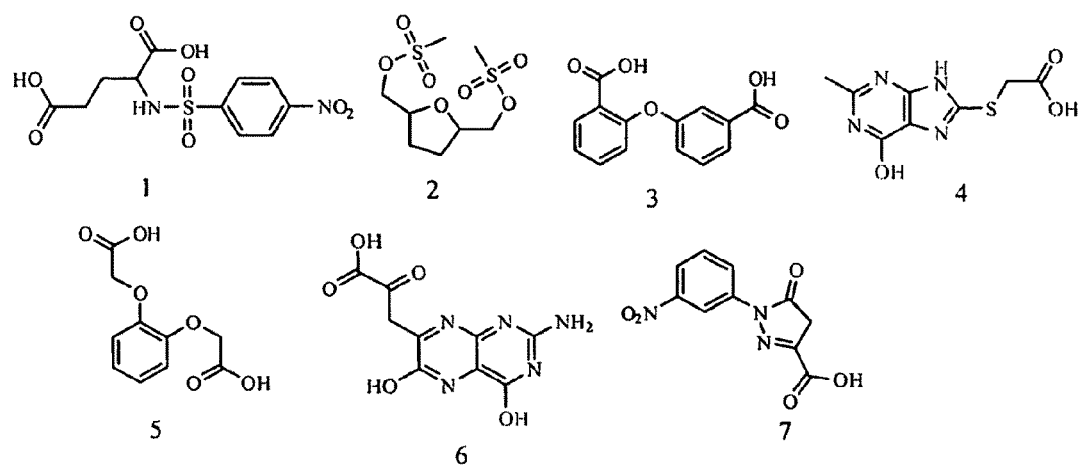
FIG. 8 shows compounds tested for their ability to modulate (e.g., inhibit or activate) the activity of PKM2 using the assays described herein. Compounds 4 and 6 were not tested.

Five candidate compounds (compounds 1, 2, 3, 5, and 7) were tested for their ability to modulate (e.g., activate or inhibit) the activity of PKM2 (FIG. 8). The compounds were synthesized as described previously in Kharalkar et al. (*Chem Biodivers*. 4: 2603-2617, 2007), hereby incorporated by reference.

For the inhibition assays, a candidate compound (2 µl 100×) was added into a well. In a control well, 2 µl of DMSO was added in place of the candidate compound. A mixture containing PKM2 (4 nM), Tris pH 7.5 (50 mM), KCl (100 mM), MgCl$_2$ (5 mM), ADP (0.6 mM), NADH (180 µM), LDH (2 units), DTT (1 µM), Tween-20 (0.01%), and DMSO (1%) was added to each well using a multi-channel pipetter at a volume of 186 µl. The mixture incubated at room temperature for 30 minutes. Immediately prior to measurement readings, 10 µl PEP (0.5 mM) and 2 µl FBP/H$_2$O (0.5 µM) were added to each well. The FBP was added in excess. Pyruvate kinase activity was measured according to published methods by a continuous assay coupled to lactate dehydrogenase (LDH). The change in absorbance at 340 nm due to oxidation of NADH was measured using a Victor$^3$ 1420 Multilabel Counter spectrophotometer (PerkinElmer, Inc.).

For the activator assays, a candidate compound (2 µl 100×) was added into a well. In a control well, 2 µl of DMSO was added in place of the candidate compound. A mixture containing PKM2 (8 nM), Tris pH 7.5 (50 mM), KCl (100 mM), MgCl$_2$ (5 mM), ADP (0.6 mM), NADH (180 µM), LDH (2 units), DTT (1 µM), Tween-20 (0.01%), and DMSO (1%) was added to each well using a multi-channel pipetter at a volume of 188 µl. The mixture incubated at room temperature for 5 minutes. Immediately prior to measurement readings, 10 µl PEP (0.5 mM) were added to each well. No FBP was added. Pyruvate kinase activity was measured according to published methods by a continuous assay coupled to LDH. The change in absorbance at 340 nm due to oxidation of NADH was measured using a Victor$^3$ 1420 Multilabel Counter spectrophotometer (PerkinElmer, Inc.).

The results of each assay are detailed in Table 1.

TABLE 1

| Compound | 1 mM Compound | 0.1 mM Compound | 0.01 mM Compound |
|---|---|---|---|
| Inhibition of PKM2 Activity | | | |
| Compound 1 | 20% | 1% | 1% |
| Compound 2 | 14% | 7% | 10% |
| Compound 3 | 20% | 1% | 1% |
| Compound 5 | 3% | 11% | 10% |
| Compound 7 | 13% | −10% | 5% |
| 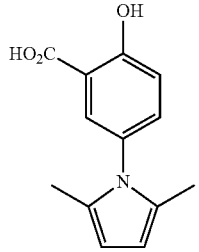 IC$_{50}$ = 130 µM | 55% | 36% | 21% |
| Activation of PKM2 Activity | | | |
| Compound 1 | −20% | −2% | −6% |
| Compound 2 | −8% | −5% | 2% |
| Compound 3 | −12% | 1% | −1% |
| Compound 5 | −10% | −15% | −15% |
| Compound 7 | 5% | −1% | −4% |
| Control (% Activation of PKM2 by FBP) | | | |
| | 1 µM | 0.3 µM | 0.1 µM |
| FBP (control) | 114% | 89% | 62% |

Other Embodiments

All publications, patents, and patent applications mentioned in this specification are herein incorporated by reference to the same extent as if each independent publication or patent application was specifically and individually indicated to be incorporated by reference.

While the invention has been described in connection with specific embodiments thereof, it will be understood that it is capable of further modifications and this application is intended to cover any variations, uses, or adaptations of the invention following, in general, the principles of the invention and including such departures from the present disclosure that come within known or customary practice within the art to which the invention pertains and may be applied to the essential features hereinbefore set forth, and follows in the scope of the claims.

Other embodiments are within the claims.

What is claimed is:

1. A method of treating a patient suffering from lung cancer, said method comprising administering to said patient in need thereof a pharmaceutical composition comprising an effective amount of a compound selected from

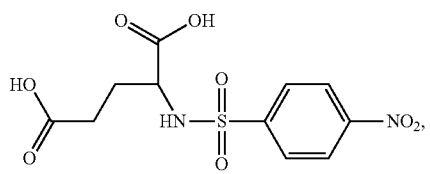

-continued

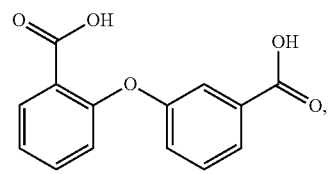

-continued

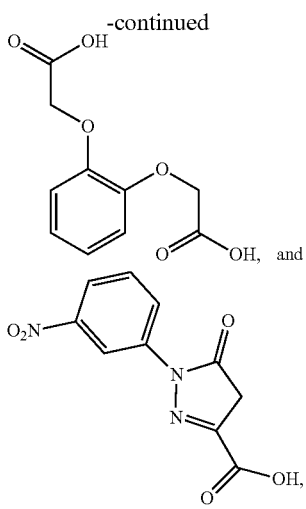

or a salt thereof, wherein said compound is administered to said patient in the absence of therapeutic levels of a hypoxic sensitizer in said patient; and further comprising administering to said patient cisplatinum to thereby treat said patient.

2. The method of claim 1, further comprising the step of identifying said patient to treat on the basis of PKM2 activity in said patient.

3. The method of claim 1 or 2, wherein said compound selectively activates PKM2.

4. The method of claim 1, wherein the compound is

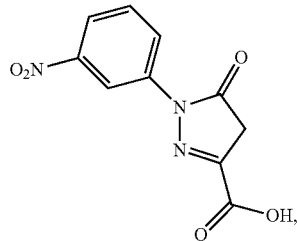 [SMILES: O=C(O)C1=NN(c2cccc([N+](=O)[O-])c2)C(=O)C1]

or a salt thereof.

* * * * *

SEQUENCE LISTING

```
<160> NUMBER OF SEQ ID NOS: 4

<210> SEQ ID NO 1
<211> LENGTH: 15
<212> TYPE: PRT
<213> ORGANISM: Artificial Sequence
<220> FEATURE:
<223> OTHER INFORMATION: Synthetic Construct
<220> FEATURE:
<221> NAME/KEY: PHOSPHORYLATION
<222> LOCATION: (8)..(8)

<400> SEQUENCE: 1

Gly Gly Ala Val Asp Asp Asp Tyr Ala Gln Phe Ala Asn Gly Gly
1               5                   10                  15

<210> SEQ ID NO 2
<211> LENGTH: 15
<212> TYPE: PRT
<213> ORGANISM: Artificial Sequence
<220> FEATURE:
<223> OTHER INFORMATION: Synthetic Construct

<400> SEQUENCE: 2

Gly Gly Ala Val Asp Asp Asp Tyr Ala Gln Phe Ala Asn Gly Gly
1               5                   10                  15

<210> SEQ ID NO 3
<211> LENGTH: 58
<212> TYPE: DNA
<213> ORGANISM: Artificial Sequence
<220> FEATURE:
<223> OTHER INFORMATION: Synthetic Construct

<400> SEQUENCE: 3
ccgggctgtg gctctagaca ctaaactcga gtttagtgtc tagagccaca gcttttttg      58

<210> SEQ ID NO 4
<211> LENGTH: 58
<212> TYPE: DNA
<213> ORGANISM: Artificial Sequence
<220> FEATURE:
<223> OTHER INFORMATION: Synthetic Construct

<400> SEQUENCE: 4
ccgggaggct tcttataagt gtttactcga gtaaacactt ataagaagcc tcttttttg      58
```